(12) United States Patent
Xu et al.

(10) Patent No.: US 10,875,926 B2
(45) Date of Patent: Dec. 29, 2020

(54) FULLY HUMAN ANTIBODY AGAINST HUMAN CD 137

(71) Applicant: Dingfu Biotarget Co., Ltd., Jiangsu (CN)

(72) Inventors: Ting Xu, Jiangsu (CN); Yan Luan, Jiangsu (CN); Xiaoxiao Wang, Jiangsu (CN); Jianjian Peng, Jiangsu (CN); Shuli Ma, Jiangsu (CN); Hui Ma, Jiangsu (CN); Xiaolong Pan, Jiangsu (CN); Shilong Fu, Jiangsu (CN); Shanshan Ning, Jiangsu (CN); Yeqiong Fei, Jiangsu (CN); Meng Zhao, Jiangsu (CN)

(73) Assignee: Dingfu Biotarget Co., Ltd., Jiangsu (CN)

( * ) Notice: Subject to any disclaimer, the term of this patent is extended or adjusted under 35 U.S.C. 154(b) by 203 days.

(21) Appl. No.: 15/761,992

(22) PCT Filed: Sep. 22, 2015

(86) PCT No.: PCT/CN2015/090226
§ 371 (c)(1),
(2) Date: Mar. 21, 2018

(87) PCT Pub. No.: WO2017/049452
PCT Pub. Date: Mar. 30, 2017

(65) Prior Publication Data
US 2018/0282422 A1    Oct. 4, 2018

(51) Int. Cl.
| | |
|---|---|
| *A61K 39/395* | (2006.01) |
| *C07K 16/28* | (2006.01) |
| *C12N 15/13* | (2006.01) |
| *C12N 15/12* | (2006.01) |
| *A61K 45/06* | (2006.01) |
| *A61P 35/00* | (2006.01) |

(52) U.S. Cl.
CPC ........ *C07K 16/2878* (2013.01); *A61K 39/395* (2013.01); *A61K 45/06* (2013.01); *C07K 16/28* (2013.01); *A61P 35/00* (2018.01); *C07K 2317/31* (2013.01); *C07K 2317/565* (2013.01); *C07K 2317/622* (2013.01); *C07K 2317/74* (2013.01); *C07K 2317/75* (2013.01)

(58) Field of Classification Search
None
See application file for complete search history.

(56) References Cited

FOREIGN PATENT DOCUMENTS

| CN | 1357009 A | 7/2002 |
|---|---|---|
| CN | 1867585 A | 11/2006 |
| JP | 2007532095 A | 11/2007 |
| JP | 2013544756 A | 12/2013 |
| WO | 0029445 A1 | 5/2000 |
| WO | 2005035584 A1 | 4/2005 |
| WO | 2006088447 | 8/2006 |

OTHER PUBLICATIONS

Chu et al., International Journal of Molecular Sciences 2019, 20, 1822; pp. 1-17. (Year: 2019).*
Qi et al., Nature Communications 201910:2141; doi.org/s41467-019-10088-1; nature.com/naturecommunications; pp. 1-11. (Year: 2019).*
Fisher, Timothy S. et al; Targeting of 4-1BB by monoclonal antibody PF-05082566 enhances T-cell function and promotes antitumor activity; Cancer Immunology, Immunotherapy, vol. 61, No. 10, Mar. 11, 2012, pp. 1721-1733, XP55391951, Berlin/Heidelberg, ISSN 0340-7004.
PCT/CN2015/090226 International Search Report dated Jun. 22, 2016.
Croft, Michael; The Role of TNF Superfamily Members in T-Cell Function and Diseases; Nature Reviews Immunology; Macmillan Publishers Ltd.; vol. 9; Apr. 2009; pp. 271-285.
Kwon, Byoung S. et al; cDNA Sequences of Two Inducible T-Cell Genes; Proc Natl Acad Sci USA; vol. 86, pp. 1963-1967; Mar. 1989; Immunology.
Laderach, Diego et al; 4-1BB Co-Stimulation Enhances Human CD8+ T Cell Priming by Augmenting the Proliferation and Survival of Effector CD8+ T Cells; Intl Immunology, vol. 14, No. 10, pp. 1155-1167; Japanese Soc for Immunology; Jul. 2002.
Melero, Ignacio et al; Monoclonal Antibodies Against the 4-1BB T-Cell Activation Molecule Eradicate Established Tumors; Nature Medicine, vol. 3, No. 6, Jun. 1997, Nature Publishing Grp; pp. 682-685.
Pollok, Karen E. et al; 4-1BB T-Cell Antigen Binds to Mature B Cells and Macrophages, and Costimulates Anti-µ-Primed Splenic B Cells; European J Immunol, 1994, 24:367-374; VCH Verlagsgesellschaft mbH 0014-2980/94/0202-0367.
Shi, Wenyin et al; Augmented Antitumor Effects of Radiation Therapy by 4-1BB Antibody (BMS-436492) Treatment; Anticancer Research, 26: 3445-3454; 2006; 0250-7005/2006.

* cited by examiner

*Primary Examiner* — Phillip Gambel
(74) *Attorney, Agent, or Firm* — Honigman LLP; Thomas A. Wootton, Esq.; Jonathan P. O'Brien

(57) ABSTRACT

Disclosed are a fully human monoclonal antibody specifically binding to a CD137 or an antigen binding portion thereof. On one hand, provided are a CDR/variable region sequence of the antibody and an encoding nucleic acid sequence thereof; on the other hand, provided is a method for treating diseases using the antibody or the antigen binding portion thereof. a fully human monoclonal antibody specifically binding to a CD137 or an antigen binding portion thereof. On one hand, provided are a CDR/variable region sequence of the antibody and an encoding nucleic acid sequence thereof; on the other hand, provided is a method for treating diseases using the antibody or the antigen binding portion thereof.

13 Claims, 19 Drawing Sheets

Specification includes a Sequence Listing.

SEQUENCE LISTING

```
<160> NUMBER OF SEQ ID NOS: 44

<210> SEQ ID NO 1
<211> LENGTH: 15
<212> TYPE: PRT
<213> ORGANISM: Artificial Sequence
<220> FEATURE:
<223> OTHER INFORMATION: linker peptide

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 22
<212> TYPE: DNA
<213> ORGANISM: Artificial Sequence
<220> FEATURE:
<223> OTHER INFORMATION: PCT primer

<400> SEQUENCE: 2
cgtagaatcg agaccgagga ga                                                  22

<210> SEQ ID NO 3
<211> LENGTH: 23
<212> TYPE: DNA
<213> ORGANISM: Artificial Sequence
<220> FEATURE:
<223> OTHER INFORMATION: PCT primer

<400> SEQUENCE: 3
ctggtggtgg tggttctgct agc                                                 23

<210> SEQ ID NO 4
<211> LENGTH: 124
<212> TYPE: PRT
<213> ORGANISM: Homo sapiens

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Ala Ser Gly Ser Thr Ile Tyr Tyr Ala Asp
    50                  55                  60

Ser Val Lys Gly Arg Phe Thr Ile Ser Arg Asp Asn Ala Asn Asn Ser
65                  70                  75                  80

Leu Tyr Leu His Met Asp Ser Leu Arg Ala Glu Asp Thr Ala Ile Tyr
                85                  90                  95

Phe Cys Ala Arg Val Val Pro Ala Gly Ser Gly Trp Arg Trp Phe Asp
            100                 105                 110
```

Pro Trp Gly Gln Gly Thr Leu Val Thr Val Ser Ser
        115                 120

<210> SEQ ID NO 5
<211> LENGTH: 5
<212> TYPE: PRT
<213> ORGANISM: Homo sapiens

<400> SEQUENCE: 5

Asp Tyr Tyr Met Asn
1               5

<210> SEQ ID NO 6
<211> LENGTH: 16
<212> TYPE: PRT
<213> ORGANISM: Homo sapiens

<400> SEQUENCE: 6

Tyr Ile Ser Ser Ser Ala Ser Gly Ser Thr Ile Tyr Tyr Ala Asp Ser
1               5                   10                  15

<210> SEQ ID NO 7
<211> LENGTH: 13
<212> TYPE: PRT
<213> ORGANISM: Homo sapiens

<400> SEQUENCE: 7

Val Val Pro Ala Gly Ser Gly Trp Arg Trp Phe Asp Pro
1               5                   10

<210> SEQ ID NO 8
<211> LENGTH: 372
<212> TYPE: DNA
<213> ORGANISM: Homo sapiens

<400> SEQUENCE: 8
gaggtgcagc tggtggagtc tgggggaggc ttggtacagc ctggagggtc cctgagactc     60
tcctgtgcag cctctggatt caccgtcagt gactactaca tgaactggat ccgccaggct    120
ccagggaagg gcctggagtg ggtttcatac attagtagta gtgctagtgg tagtaccata    180
tactacgcag actctgtgaa gggccgattc accatctcca gggacaacgc caacaactca    240
ctgtatctgc acatggacag cctgagagcc gaggacacgg ccatatactt ctgtgcgaga    300
gtcgtcccag ctggaagtgg gtggaggtgg ttcgacccct ggggccaggg taccctggtc    360
actgtctcct ca                                                        372

<210> SEQ ID NO 9
<211> LENGTH: 111
<212> TYPE: PRT
<213> ORGANISM: Homo sapiens

<400> SEQUENCE: 9

Gln Ser Val Leu Ile Gln Pro Pro Ser Ala Ser Gly Ser Pro Gly Gln
1               5                   10                  15

Ser Val Thr Ile Ser Cys Thr Gly Ile Ser Ser Asp Val Gly Ala Tyr
            20                  25                  30

Asp Tyr Val Ser Trp Tyr Gln Gln His Pro Gly Lys Val Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asp Thr Ala Ser Leu Thr Val Ser Gly Leu
65                  70                  75                  80

Gln Ala Glu Asp Glu Ala Asp Tyr Tyr Cys Ser Ser His Ala Gly Ser
                85                  90                  95

Asn Asn Phe Tyr Val Phe Gly Thr Gly Thr Lys Leu Thr Val Leu
            100                 105                 110

<210> SEQ ID NO 10
<211> LENGTH: 14
<212> TYPE: PRT
<213> ORGANISM: Homo sapiens

<400> SEQUENCE: 10

Thr Gly Ile Ser Ser Asp Val Gly Ala Tyr Asp Tyr Val Ser
1               5                   10

<210> SEQ ID NO 11
<211> LENGTH: 7
<212> TYPE: PRT
<213> ORGANISM: Homo sapiens

<400> SEQUENCE: 11

Glu Val Ser Lys Arg Pro Ser
1               5

<210> SEQ ID NO 12
<211> LENGTH: 11
<212> TYPE: PRT
<213> ORGANISM: Homo sapiens

<400> SEQUENCE: 12

Ser Ser His Ala Gly Ser Asn Asn Phe Tyr Val
1               5                   10

<210> SEQ ID NO 13
<211> LENGTH: 333
<212> TYPE: DNA
<213> ORGANISM: Homo sapiens

<400> SEQUENCE: 13
cagtctgttc tgattcagcc tccctccgcg tccgggtctc ctggacagtc agtcaccatc     60
tcctgcactg gaatcagcag tgacgttggt gcttatgact atgtctcctg gtaccaacag    120
cacccaggca aagtccccaa actcatgatt tatgaggtca gtaagcggcc ctcaggggtc    180
cctgatcgct tctctggctc caagtctggc gacacggcct ccctgaccgt ctctgggctc    240
caggctgagg atgaggctga ttactactgc agctcacatg caggcagcaa caattttat    300
gtcttcggaa ctgggaccaa gctgaccgtc cta                                 333

<210> SEQ ID NO 14
<211> LENGTH: 123
<212> TYPE: PRT
<213> ORGANISM: Homo sapiens

<400> SEQUENCE: 14

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Pro Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120

<210> SEQ ID NO 15
<211> LENGTH: 7
<212> TYPE: PRT
<213> ORGANISM: Homo sapiens

<400> SEQUENCE: 15

Ser Asn Ser Ala Ala Trp Asn
1               5

<210> SEQ ID NO 16
<211> LENGTH: 18
<212> TYPE: PRT
<213> ORGANISM: Homo sapiens

<400> SEQUENCE: 16

Arg Thr Tyr Tyr Arg Ser Lys Trp Tyr Asn Asp Tyr Ala Pro Ser Val
1               5                   10                  15

Glu Ser

<210> SEQ ID NO 17
<211> LENGTH: 11
<212> TYPE: PRT
<213> ORGANISM: Homo sapiens

<400> SEQUENCE: 17

Asp Pro Pro Tyr Val Leu Ser Thr Phe Asp Ile
1               5                   10

<210> SEQ ID NO 18
<211> LENGTH: 369
<212> TYPE: DNA
<213> ORGANISM: Homo sapiens

<400> SEQUENCE: 18
caggtacagc tgcagcagtc aggtccagga ctggtgaagc cctcgcagac cctctcactc        60
acctgtgcca tctccgggga cagtgtttct agcaacagtg ctgcttggaa ctggatcagg       120
cagtccccat cgaggggcct tgagtggctg ggaaggacat actacaggtc caagtggtat       180
aatgattatg caccatctgt ggaaagtcga ataaccatca cccagacac atccaagaac       240 cagttctccc tgcagctgag ctctgtgact cccgaggaca cggctgtgta ctactgtgca       300
agagaccctc cttatgtgct cagtactttt gatatctggg gccaagggac aatggtcacc       360
gtctcctca                                                               369

<210> SEQ ID NO 19
<211> LENGTH: 110
<212> TYPE: PRT
<213> ORGANISM: Homo sapiens

<400> SEQUENCE: 19

```
Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Thr
                85                  90                  95

Asn Asn Val Ile Phe Gly Gly Gly Thr Lys Leu Thr Val Leu
            100                 105                 110

<210> SEQ ID NO 20
<211> LENGTH: 13
<212> TYPE: PRT
<213> ORGANISM: Homo sapiens

<400> SEQUENCE: 20

Thr Arg Ser Ser Gly Asn Ile Ala Ser Phe Tyr Val Gln
1               5                   10

<210> SEQ ID NO 21
<211> LENGTH: 7
<212> TYPE: PRT
<213> ORGANISM: Homo sapiens

<400> SEQUENCE: 21

Glu Asp Asp Gln Arg Pro Ser
1               5

<210> SEQ ID NO 22
<211> LENGTH: 9
<212> TYPE: PRT
<213> ORGANISM: Homo sapiens

<400> SEQUENCE: 22

Gln Ser Tyr Asp Thr Asn Asn Val Ile
1               5

<210> SEQ ID NO 23
<211> LENGTH: 330
<212> TYPE: DNA
<213> ORGANISM: Homo sapiens

<400> SEQUENCE: 23
aattttatgc tgactcagcc ccctctgtgt cggagtccc  ggggaagac ggtaaccatc      60 tcctgcaccc gcagcagtgg gaacattgcc agcttctatg tgcagtggtt tcaacagcgc    120
ccgggcagtt cccccaccac tgtgatctat gaagatgacc aaagaccctc tggggtccct    180
gatcggttct ctggctccat cgacagatcg tccaactctg cctccctcac catttctgga    240
ctgacgactg acgacgaggc tgactactac tgtcagtctt atgataccaa caatgtcata    300
ttcggcggag ggaccaagct gaccgtccta                                     330

<210> SEQ ID NO 24
<211> LENGTH: 24
<212> TYPE: DNA
```

```
<213> ORGANISM: Artificial Sequence
<220> FEATURE:
<223> OTHER INFORMATION: Plasmid

<400> SEQUENCE: 24
tctggtggtg gtggttctgc tagc                                               24

<210> SEQ ID NO 25
<211> LENGTH: 59
<212> TYPE: DNA
<213> ORGANISM: Artificial Sequence
<220> FEATURE:
<223> OTHER INFORMATION: Primer

<400> SEQUENCE: 25
gccagatctc gagctattac aagtcttctt cagaaataag cttttgttct agaattccg         59

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
taatacgact cactataggg                                                    20

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
ggcagcccca taaacacaca gtat                                               24

<210> SEQ ID NO 28
<211> LENGTH: 123
<212> TYPE: PRT
<213> ORGANISM: Homo sapiens

<400> SEQUENCE: 28

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Arg Trp Tyr Ser Asp Tyr Ala
    50                  55                  60

Ser Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120

<210> SEQ ID NO 29
<211> LENGTH: 18
```

```
<212> TYPE: PRT
<213> ORGANISM: Homo sapiens

<400> SEQUENCE: 29

Arg Thr Tyr Tyr Arg Ser Arg Trp Tyr Ser Asp Tyr Ala Ser Ser Val
1               5                   10                  15

Glu Ser

<210> SEQ ID NO 30
<211> LENGTH: 369
<212> TYPE: DNA
<213> ORGANISM: Homo sapiens

<400> SEQUENCE: 30
caggtacagc tgcagcagtc aggtccagga ctggtgaagc cctcgcagac cctctcactc      60
acctgtgcca tctccgggga cagtgtttct agcaacagtg ctgcttggaa ctggatcagg     120
cagtccccat cgaggggcct tgagtggctg gaaggacat actacaggtc caggtggtat      180
agtgattatg catcatctgt ggaaagtcga ataaccatca acccagacac atccaagaac    240
cagttctccc tgcagctgag ctctgtgact cccgaggaca cggctgtgta ctactgtgca    300
agagaccctc cttatgtgct cagtactttt gatatctggg gccaagggac aatggtcacc    360
gtctcctca                                                             369

<210> SEQ ID NO 31
<211> LENGTH: 123
<212> TYPE: PRT
<213> ORGANISM: Homo sapiens

<400> SEQUENCE: 31

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Pro Ser Val Glu Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Asp Pro Pro Tyr Val Leu Ser Thr Phe Asp Ile
            100                 105                 110

Trp Gly Gln Gly Thr Met Val Thr Val Ser Ser
        115                 120

<210> SEQ ID NO 32
<211> LENGTH: 7
<212> TYPE: PRT
<213> ORGANISM: Homo sapiens

<400> SEQUENCE: 32

Ser Asp Ser Ala Ala Trp Asn
1               5

<210> SEQ ID NO 33
<211> LENGTH: 369
<212> TYPE: DNA
```

<213> ORGANISM: Homo sapiens

<400> SEQUENCE: 33

```
caggtacagc tgcagcagtc aggtccagga ctggtgaagc cctcgcagac cctctcactc    60
acctgtgcca tctccgggga cagtgttttct agcgacagtg ctgcttggaa ctggatcagg   120
cagtccccat cgaggggcct tgagtggctg ggaaggacat actacaggtc caagtggtat   180
aatgattatg caccatctgt ggaaagtcga ataaccatca acccagacac atccaagaac   240
cagttctccc tgcagctgag ctctgtgact cccgaggaca cggctgtgta ctactgtgca   300
agagaccctc cttatgtgct cagtactttt gatatctggg ccaagggac aatggtcacc    360
gtctcctca                                                          369
```

<210> SEQ ID NO 34
<211> LENGTH: 110
<212> TYPE: PRT
<213> ORGANISM: Homo sapiens

<400> SEQUENCE: 34

```
Asn Phe Met Leu Thr Gln Pro Pro Ser Val Ser Glu Ser Pro Gly Lys
1               5                   10                  15
Thr Val Thr Ile Ser Cys Thr Arg Ser Ser Gly Asn Ile Ala Ser Phe
            20                  25                  30
Tyr Val Gln Trp Phe Gln Gln Arg Pro Gly Ser Ser Pro Thr Thr Val
        35                  40                  45
Ile Tyr Asp Asp Asp Gln Arg Pro Ser Gly Val Pro Asp Arg Phe Ser
    50                  55                  60
Gly Ser Ile Asp Arg Ser Ser Asn Ser Ala Ser Leu Thr Ile Ser Gly
65                  70                  75                  80
Leu Thr Thr Asp Asp Glu Ala Asp Tyr Tyr Cys Gln Ser Tyr Asp Thr
                85                  90                  95
Asn Asn Val Ile Phe Gly Gly Gly Thr Lys Leu Thr Val Leu
            100                 105                 110
```

<210> SEQ ID NO 35
<211> LENGTH: 7
<212> TYPE: PRT
<213> ORGANISM: Homo sapiens

<400> SEQUENCE: 35

```
Asp Asp Asp Gln Arg Pro Ser
1               5
```

<210> SEQ ID NO 36
<211> LENGTH: 330
<212> TYPE: DNA
<213> ORGANISM: Homo sapiens

<400> SEQUENCE: 36

```
aattttatgc tgactcagcc cccctctgtg tcggagtccc cggggaagac ggtaaccatc    60
tcctgcaccc gcagcagtgg gaacattgcc agcttctatg tgcagtggtt tcaacagcgc   120
ccgggcagtt cccccaccac tgtgatctat gacgatgacc aaagaccctc tggggtccct   180
gatcggttct ctggctccat cgacagatcg tccaactctg cctccctcac catttctgga   240
ctgacgactg acgacgaggc tgactactac tgtcagtctt atgataccaa caatgtcata   300
ttcggcggag ggaccaagct gaccgtccta                                    330
```

```
<210> SEQ ID NO 37
<211> LENGTH: 110
<212> TYPE: PRT
<213> ORGANISM: Homo sapiens

<400> SEQUENCE: 37

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
50                  55                  60

Gly Ser Ile Asp Arg Ser Ser Asn Ser Ala Ser Leu Thr Ile Ser Gly
65                  70                  75                  80

Leu Thr Thr Asp Asp Glu Ala Asp Tyr Tyr Cys Gln Ser Tyr Asp Thr
                85                  90                  95

Asn Lys Val Ile Phe Gly Gly Gly Thr Lys Leu Thr Val Leu
            100                 105                 110

<210> SEQ ID NO 38
<211> LENGTH: 9
<212> TYPE: PRT
<213> ORGANISM: Homo sapiens

<400> SEQUENCE: 38

Gln Ser Tyr Asp Thr Asn Lys Val Ile
1               5

<210> SEQ ID NO 39
<211> LENGTH: 330
<212> TYPE: DNA
<213> ORGANISM: Homo sapiens

<400> SEQUENCE: 39
aattttatgc tgactcagcc ccctctgtg tcggagtccc cggggaagac ggtaaccatc      60
tcctgcaccc gcagcagtgg gaacattgcc agcttctatg tgcagtggtt tcaacagcgc     120
ccgggcagtt cccccaccac tgtgatctat gaagatgacc aaagaccctc tggggtccct     180
gatcggttct ctggctccat cgacagatcg tccaactctg cctccctcac catttctgga     240
ctgacgactg acgacgaggc tgactactac tgtcagtctt atgataccaa caaggtcata     300
ttcggcggag ggaccaagct gaccgtccta                                      330

<210> SEQ ID NO 40
<211> LENGTH: 110
<212> TYPE: PRT
<213> ORGANISM: Homo sapiens

<400> SEQUENCE: 40

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
50                  55                  60
```

-continued

Gly Ser Ile Asp Arg Ser Ser Asn Ser Ala Ser Leu Thr Ile Ser Gly
 65                  70                  75                  80

Leu Thr Thr Asp Asp Glu Ala Asp Tyr Tyr Cys Gln Ser Tyr Asp Ile
                 85                  90                  95

Asn Lys Val Ile Phe Gly Gly Gly Thr Lys Leu Thr Val Leu
            100                 105                 110

<210> SEQ ID NO 41
<211> LENGTH: 9
<212> TYPE: PRT
<213> ORGANISM: Homo sapiens

<400> SEQUENCE: 41

Gln Ser Tyr Asp Ile Asn Lys Val Ile
1               5

<210> SEQ ID NO 42
<211> LENGTH: 330
<212> TYPE: DNA
<213> ORGANISM: Homo sapiens

<400> SEQUENCE: 42
aattttatgc tgactcagcc cccctctgtg tcggagtccc cggggaagac ggtaaccatc      60
tcctgcaccc gcagcagtgg gaacattgcc agcttctatg tgcagtggtt caacagcgc     120 ccgggcagtt cccccaccac tgtgatctat gaagatgacc aaagacccct cggggtccct     180
gatcggttct ctggctccat cgacagatcg tccaactctg cctccctcac catttctgga     240
ctgacgactg acgacgaggc tgactactac tgtcagtctt atgatatcaa caaggtcata     300
ttcggcggag ggaccaagct gaccgtccta                                      330

<210> SEQ ID NO 43
<211> LENGTH: 110
<212> TYPE: PRT
<213> ORGANISM: Homo sapiens

<400> SEQUENCE: 43

Asn Phe Met Leu Thr Gln Pro Pro Ser Val Ser Glu Ser Pro Gly Lys
1               5                   10                  15

Thr Val Thr Ile Ser Cys Thr Arg Ser Ser Gly Asn Ile Ala Ser Phe
            20                  25                  30

Tyr Val Gln Trp Phe Gln Gln Arg Pro Gly Ser Ser Pro Thr Thr Val
        35                  40                  45

Ile Tyr Asp Asp Gln Arg Pro Ser Gly Val Pro Asp Arg Phe Ser
 50                  55                  60

Gly Ser Ile Asp Arg Ser Ser Asn Ser Ala Ser Leu Thr Ile Ser Gly
 65                  70                  75                  80

Leu Thr Thr Asp Asp Glu Ala Asp Tyr Tyr Cys Gln Ser Tyr Asp Ile
                 85                  90                  95

Asn Lys Val Ile Phe Gly Gly Gly Thr Lys Leu Thr Val Leu
            100                 105                 110

<210> SEQ ID NO 44
<211> LENGTH: 330
<212> TYPE: DNA
<213> ORGANISM: Homo sapiens

<400> SEQUENCE: 44
aattttatgc tgactcagcc cccctctgtg tcggagtccc cggggaagac ggtaaccatc      60

```
tcctgcaccc gcagcagtgg gaacattgcc agcttctatg tgcagtggtt tcaacagcgc    120
ccgggcagtt cccccaccac tgtgatctat gacgatgacc aaagaccctc tggggtccct    180
gatcggttct ctggctccat cgacagatcg tccaactctg cctccctcac catttctgga    240
ctgacgactg acgacgaggc tgactactac tgtcagtctt atgatatcaa caaggtcata    300
ttcggcggag ggaccaagct gaccgtccta                                     330
```

FULLY HUMAN ANTIBODY AGAINST HUMAN CD 137

CROSS-REFERENCE TO RELATED APPLICATIONS

This application claims priority under 35 U.S.C. § 371 to Patent Cooperation Treaty application PCT/CN2015/090226, filed Sep. 22, 2015, the entire contents of which are incorporated herein by reference.

SEQUENCE LISTING

This application incorporates in its entirety the Sequence Listing entitled "262790-425455_Sequence_Listing_ST25.txt" (20,808 bytes), which was created on Mar. 21, 2018 and filed electronically herewith.

FIELD OF THE INVENTION

The present invention relates to a complete human antibody. Specifically, the present invention relates to a fully human antibody against human CD 137 and use thereof.

BACKGROUND OF THE INVENTION

CD137 (also known as 4-1BB, TNFRSF9, etc.) is a member of the superfamily of tumor necrosis factor receptors, belonging to type-I transmembrane protein. The human CD137, which is a protein comprising 255 amino acids (Uniport: Q07011) of 30 KD, is usually expressed on the cell membrane in the form of a homodimer of 55 KD and will have tripolyzation under the induction of the ligand so as to initiate cell signal conduction. CD137L is a member of the superfamily of tumor necrosis factor receptors, belonging to type-II transmembrane protein.

The current research results showed that, CD137L is mainly expressed on activated APCs, such as dendritic cells (DC), macrophages and B cells (Pollok, K. E. et al., 1994, Eur. J. Immunol. 24: 367-74); while CD137 may be induced to express after T cells receive the antigen-specific signals (Kwon, B. S. et al., 1989, PNAS 86:1963-67).

The function of CD137 on T cells has been well proved. In the presence of a certain amount of CD3 antibody, activation of CD137 signals may induce the proliferation of T cells and the synthesis of cytokines (mainly IFN-γ), and inhibits the apoptosis of activated T cells, thereby prolonging the life of T cells (D. Laderach et al., 2002, Int.mmunol., 14(10): 1155-67; Croft et al., 2009, Nat Rev Immunol 19:271-285). A research result showed that CD137 agonist mAb can enhance the killing capability of T lymphocytes in many mice tumor models, leading to an anti-tumor effect (Melero, I. et al., 1997, Nat. Med., 3:682-85). Meanwhile, the combination administration of an approved cancer treatment method and a CD137 agonist mAb had achieved an exciting result. The research result of SHI et al. (Shi. W. et al., 2006, Anticancer Res., 26:3445-53) showed that the combination administration of CD137 agonist (Agonist) and radiotherapy can significantly inhibit the growth of large tumors.

Therefore, based on the effect of CD137 in tumor immunotherapy, a fully human antibody against human CD 137 with an active effect is needed for treating and preventing human diseases such as cancer, tumors, infectious diseases and autoimmune diseases.

SUMMARY OF THE INVENTION

The present invention provides a monoclonal antibody specifically binding to CD137 or an antigen-binding portion thereof, comprising a heavy chain variable region and a light chain variable region, wherein:

said heavy chain variable region comprises a CDR1 having a sequence as set forth in SEQ ID NO.5, a CDR2 having a sequence as set forth in SEQ ID NO.6, and a CDR3 having a sequence as set forth in SEQ ID NO.7; and said light chain variable region comprises a CDR1 having a sequence as set forth in SEQ ID NO.10, a CDR2 having a sequence as set forth in SEQ ID NO.11, and a CDR3 having a sequence as set forth in SEQ ID NO.12;

or said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.22;

or said heavy chain variable region comprises a CDR1 having a sequence as set forth in SEQ ID NO.15, a CDR2 having a sequence as set forth in SEQ ID NO.29, and a CDR3 having a sequence as set forth in SEQ ID NO.17; and said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.22;

or said heavy chain variable region comprises a CDR1 having a sequence as set forth in SEQ ID NO.32, a CDR2 having a sequence as set forth in SEQ ID NO.16, and a CDR3 having a sequence as set forth in SEQ ID NO.17; and said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.22;

or said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and said light chain variable region comprises a CDR1 having a sequence as set forth in SEQ ID NO.20, a CDR2 having a sequence as set forth in SEQ ID NO.35, and a CDR3 having a sequence as set forth in SEQ ID NO.22;

or said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.38;

or said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.41;

or said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and said light chain variable region comprises a CDR1 having a sequence as set forth in SEQ ID NO.20, a CDR2 having a sequence as set forth in SEQ ID NO.35, and a CDR3 having a sequence as set forth in SEQ ID NO.41.

In one aspect of the present invention, the present invention provides a monoclonal antibody specifically binding to CD137 or an antigen binding portion thereof, wherein:

said heavy chain comprises a variable region having a sequence as set forth in SEQ ID NO.4; and said light chain comprises a variable region having a sequence as set forth in SEQ ID NO.9;

or said heavy chain comprises a variable region having a sequence as set forth in SEQ ID NO.14; and said light chain comprises a variable region having a sequence as set forth in SEQ ID NO.19;

or said heavy chain comprises a variable region having a sequence as set forth in SEQ ID NO.28; and said light chain comprises a variable region having a sequence as set forth in SEQ ID NO.19;

or said heavy chain comprises a variable region having a sequence as set forth in SEQ ID NO.31; and said light chain comprises a variable region having a sequence as set forth in SEQ ID NO.19;

or said heavy chain comprises a variable region having a sequence as set forth in SEQ ID NO.14; and said light chain comprises a variable region having a sequence as set forth in SEQ ID NO.34;

or said heavy chain comprises a variable region having a sequence as set forth in SEQ ID NO.14; and said light chain comprises a variable region having a sequence as set forth in SEQ ID NO.37;

or said heavy chain comprises a variable region having a sequence as set forth in SEQ ID NO.14; and said light chain comprises a variable region having a sequence as set forth in SEQ ID NO.40;

or said heavy chain comprises a variable region having a sequence as set forth in SEQ ID NO.14; and said light chain comprises a variable region having a sequence as set forth in SEQ ID NO.43.

In yet another aspect of the present invention, the present invention provides a monoclonal antibody specifically binding to CD137 or an antigen-binding portion thereof, wherein the antibody or an antigen-binding portion thereof is a complete antibody, a bispecific antibody, scFv, Fab, Fab', F(ab')2 or Fv.

In another aspect of the present invention, the present invention provides a single-chain antibody, comprising a VH, a VL and a linker peptide, wherein the VH has a sequence as set forth in SEQ ID NO.4, the VL has a sequence as set forth in SEQ ID NO.9, and the linker peptide has a sequence as set forth in SEQ ID NO.1.

In yet another aspect of the present invention, the present invention provides a single-chain antibody, comprising a VH, a VL and a linker peptide, wherein the VH has a sequence as set forth in SEQ ID NO.14, the VL has a sequence as set forth in SEQ ID NO.23, and the linker peptide has a sequence as set forth in SEQ ID NO.1.

In another aspect of the present invention, the present invention provides a pharmaceutical composition, comprising:

the above-mentioned monoclonal antibody or an antigen-binding portion thereof; and a pharmaceutically acceptable carrier.

In yet another aspect of the present invention, the present invention provides a method for treating cancers in a subject, comprising administering to said subject a therapeutically effective amount of the above-mentioned monoclonal antibody or an antigen-binding portion thereof.

In yet another aspect of the present invention, the present invention provides a method for combined treatment of a cancer in a subject, comprising administering to said subject a therapeutically effective amount of the above-mentioned monoclonal antibody or an antigen-binding portion thereof, further comprising administering to the subject a therapeutically effective amount of additional medicaments for treating cancers or implementing other methods for treating cancers.

In particular embodiments of the present invention, the present invention provides a method for treating infectious diseases or autoimmune diseases in a subject, comprising administering to said subject a therapeutically effective amount of the above-mentioned monoclonal antibody or an antigen-binding portion thereof.

In particular embodiments of the present invention, the present invention provides a method for treating tumors in a subject, comprising administering to said subject a therapeutically effective amount of the above-mentioned monoclonal antibody or an antigen-binding portion thereof.

In particular embodiments of the present invention, the present invention provides a method for combined treatment of infectious diseases or autoimmune diseases in a subject, comprising administering to said subject a therapeutically effective amount of the above-mentioned monoclonal antibody or an antigen-binding portion thereof, further comprising administering to said subject a therapeutically effective amount of additional medicaments for treating infectious diseases or autoimmune diseases or implementing other methods for treating infectious diseases or autoimmune diseases.

In particular embodiments of the present invention, the present invention provides a combined treatment method of tumors in a subject, comprising administering to said subject a therapeutically effective amount of the above-mentioned monoclonal antibody or an antigen-binding portion thereof, further comprising administering to said subject a therapeutically effective amount of additional medicaments for treating tumors or implementing other methods for treating tumors.

Other methods for treating cancers or tumors described in the present invention include radiotherapy or other approved methods for treating cancers or tumors.

The present invention also provides an isolated polynucleotide, comprising a nucleotide sequence encoding the amino acid sequences as set forth in SEQ ID NO.4, SEQ ID NO.14, SEQ ID NO.28, and SEQ ID NO.31, or a nucleotide sequence encoding amino acid sequences with a homology of 90%, 91%, 92%, 93%, 94%, 95%, 96%, 97%, 98%, and 99%. Specifically, said isolated polynucleotide comprises nucleotide sequences as set forth in SEQ ID NO.8, SEQ ID NO.18, SEQ ID NO.30, and SEQ ID NO.33, or a nucleotide sequence with a homology of 90%, 91%, 92%, 93%, 94%, 95%, 96%, 97%, 98%, and 99%.

The present invention further provides an isolated polynucleotide, comprising a nucleotide sequence encoding amino acid sequences as set forth in SEQ ID NO.9, SEQ ID NO.19, SEQ ID NO.34, SEQ ID NO.37, SEQ ID NO.40, SEQ ID NO.43, or a nucleotide sequence encoding amino acid sequences with a homology of 90%, 91%, 92%, 93%, 94%, 95%, 96%, 97%, 98%, and 99%. Specifically, said isolated polynucleotide comprises a nucleotide sequence as set forth in SEQ ID NO.13, SEQ ID NO.23, SEQ ID NO.36, SEQ ID NO.39, SEQ ID NO.42, and SEQ ID NO.44, or a nucleotide sequence as set forth in with a homology of 90%, 91%, 92%, 93%, 94%, 95%, 96%, 97%, 98%, and 99%.

Beneficial effects of the present invention are as followings: according to the invention, an antibody capable of binding human CD137 protein was obtained through a yeast surface display technology, which is a complete human antibody, and the affinity of the antibody has been greatly enhanced.

The present invention will be described in more detail with reference to the accompanying drawings. From the following detailed description, the above-mentioned aspects of the invention and other aspects of the invention will be obvious.

DESCRIPTION OF SEQUENCES

Figure 1:
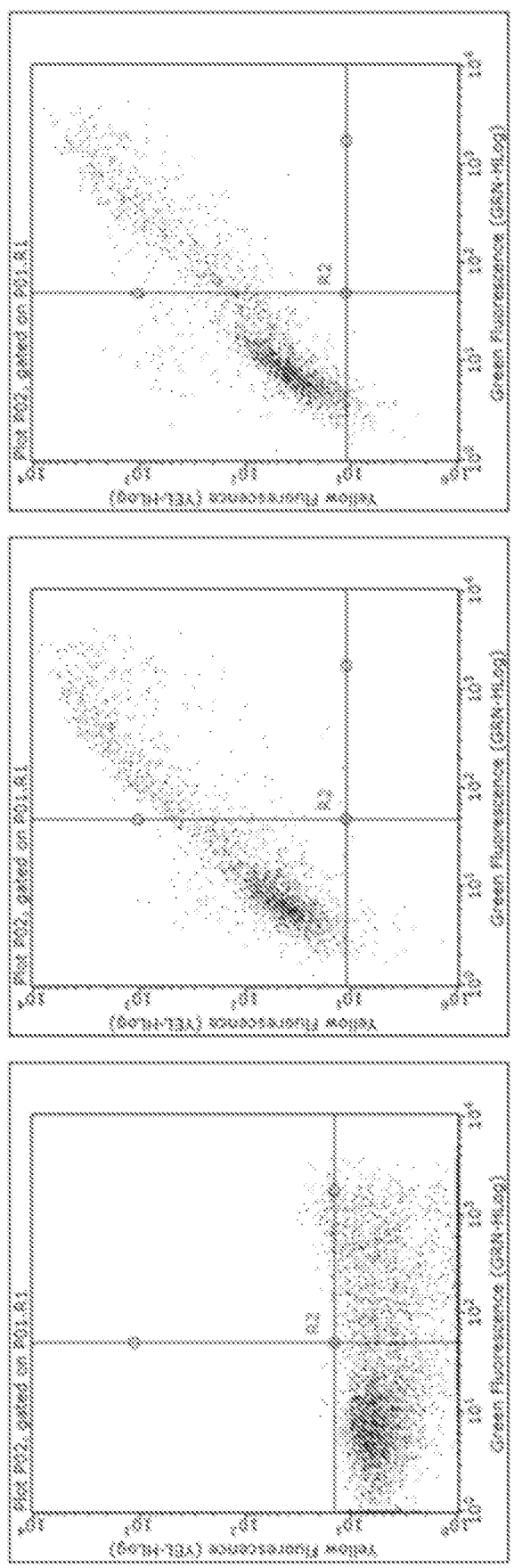
FIG. 1 is a graph showing the results of the binding of purified anti-hCD 137 scFv to hCD137-EGFP cells, where X-axis represents the fluorescence intensity of EGFP, and Y-axis represents the fluorescence intensity of anti-hIg-PE.
Figure 2A:
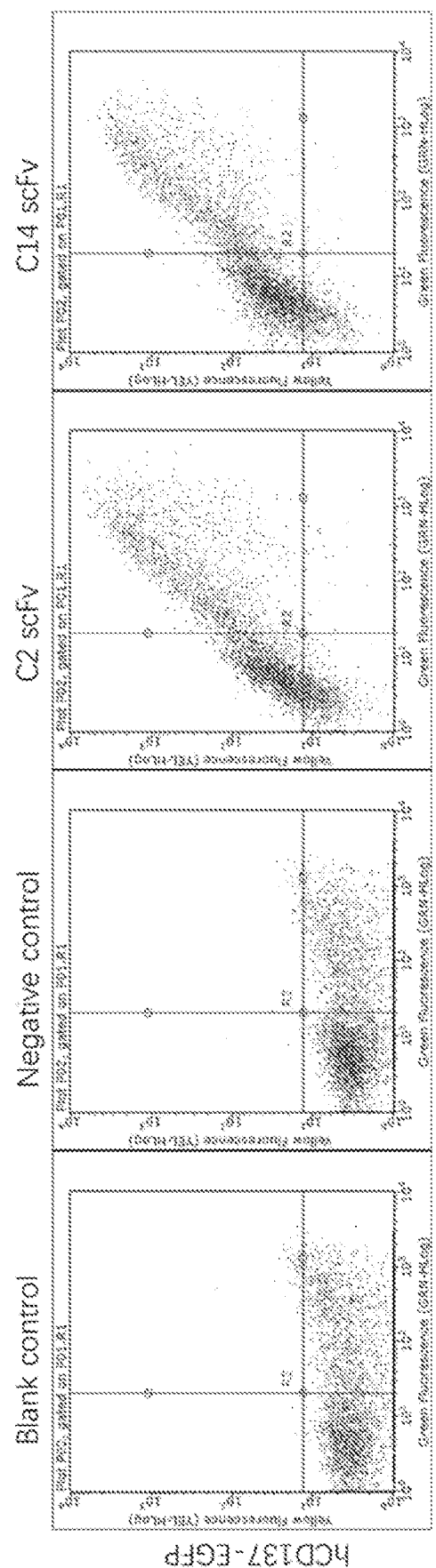
FIG. 2 is a graph showing the results of the specific binding of purified anti-hCD 137 scFv to hCD137-EGFP cells, where X-axis represents the fluorescence intensity of EGFP, and Y-axis represents the fluorescence intensity of anti-hIg-PE.
Figure 2B:
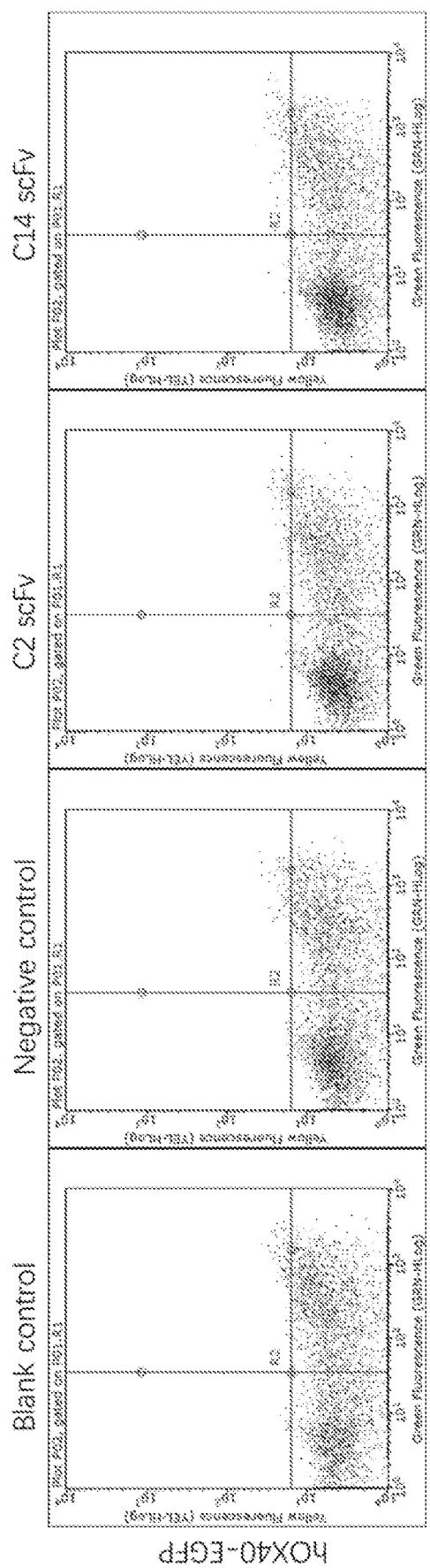
Figure 2C:
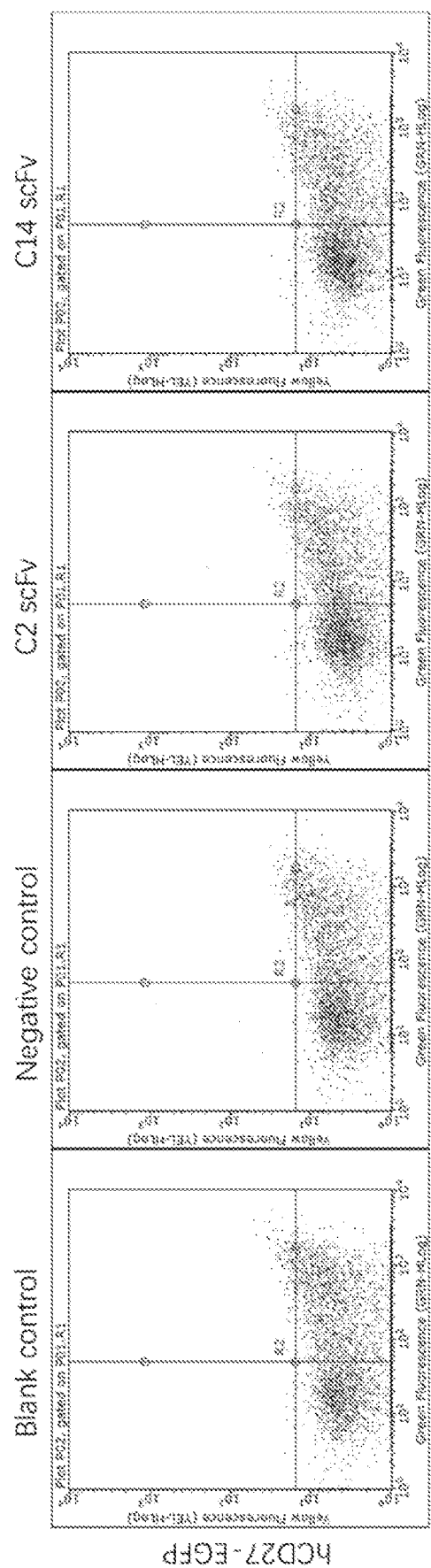
Figure 2D:
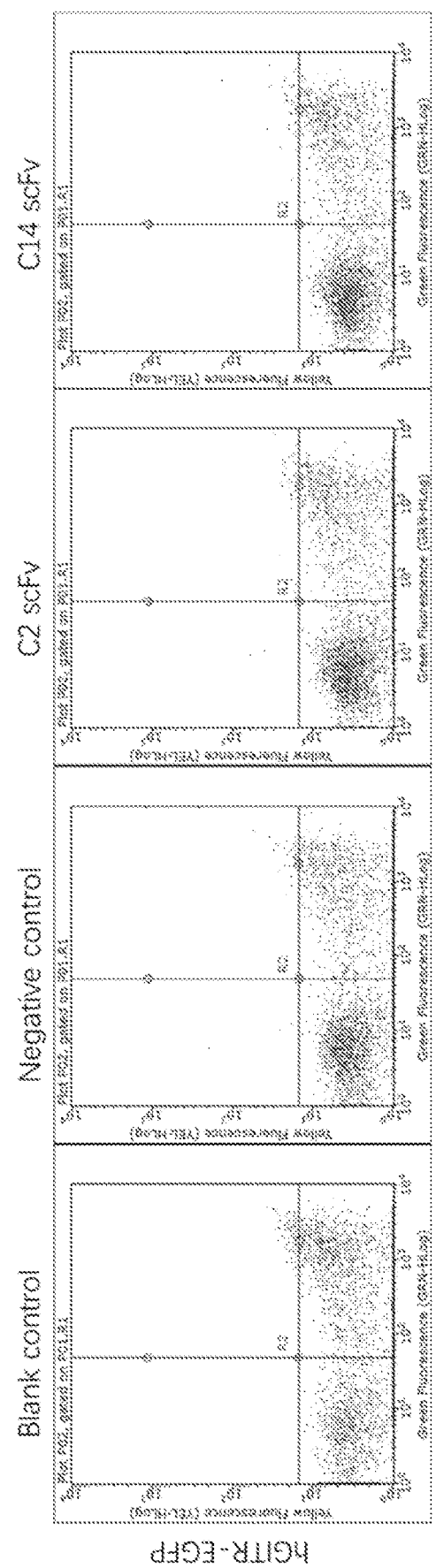

Sequences involved in the present invention include nucleotide sequences and amino acid sequences and have been summarized into a sequence list, attached followed by the specification, and meanwhile, the inventor has submitted the sequence list in a computer readable form.

DETAILED DESCRIPTION OF THE EMBODIMENTS

The present invention is not limited to specific methods, solutions, antibodies, or cell lines described herein because they may vary. In addition, the terms used herein are used only for the purpose of describing particular embodiments and are not intended to limit the scope of the present invention.

Unless otherwise defined, all technical and scientific terms and any abbreviations herein all have the same meaning as commonly understood by a person skilled in the art. Although methods and materials similar or equivalent to those described herein may be used in the practice of the invention, illustrative methods, devices, and materials are described herein.

Unless otherwise indicated, the terms in the present invention have the meanings commonly used in the art.

The term "antibody" as used in the present invention refers to any immunoglobulin or complete molecule binding to specific epitope as well as portion thereof. The antibodies include, but not limited to, polyclonal antibody, monoclonal antibody, chimeric antibody, humanized antibody, single-chain antibody, and fragments and/or portions of the complete antibody, provided that these fragments or portions remain the antigen binding capabilities of parental antibodies. For example, in the present invention, "anti-hCD137 antibody" refers to a monoclonal antibody, a polyclonal antibody, a single-chain antibody and fragments or portions thereof or functional variants or functional fragments thereof with immune activities, which was capable of specifically binding to human CD137.

The term "the position of an antibody" as used in the present invention is obtained according to the reference on a website, it does not refer to the actual positions of the amino acids in the sequence.

The term "binding" or "specifically binding" as used in the present invention refers to with a purified wild-type antigen, the binding of an antibody with the antigen epitope in the in vitro determination process, preferably in the plasmon resonance determination process (BIAcore™, GE-Healthcare™, Uppsala, Sweden).

The term "human monoclonal antibody" as used in the present invention refers to the antibody exhibiting a single binding specificity with variable and constant regions derived from human-type immunoglobulin sequences.

EXAMPLES

Example 1. Expression of Recombinant Human CD137 and Preparation of Related EGFP Cells The amino acid sequence (i.e., from the residue 1 to the residue 186 in Q07011) of the human CD137 extracellular domain was obtained according to the amino acid sequence of human CD137 in the Uniprot™ protein database; the amino acid sequence (i.e., from the residue 1 to the residue 186 in F6W5G6) of the monkey CD137 extracellular domain was obtained according to the amino acid sequence (F6W5G6) of rhesus monkey CD137 (RhCD137) in the Uniprot™ protein database; the amino acid sequence (i.e., from the residue 104 to the residue 330 in P01857) of the human IgG1-Fc domain was obtained according to the constant region amino acid sequence (P01857) of human immunoglobulin gamma (.gamma.)1 (IgG1) in the Uniprot™ protein database; the amino acid sequence (i.e., the residue 98 to the residue 324 in P01868) of mouse IgG1-Fc (muFc) domain was obtained according to the constant region amino acid sequence (P01868) of mouse immunoglobulin gamma (.gamma.)1 (IgG1) in the Uniprot™ protein database. The corresponding encoding DNA sequences were designed by using DNAworks™ online tool to obtain the genes of hCD137-Fc, hCD137-muFc and RhCD137-muFc fusion proteins. The amino acid sequence (C5MKY7) of enhanced green fluorescent protein (EGFP), the amino acid sequence (Q07011) of human CD137, the amino acid sequence (P20334) of mouse CD137, the amino acid sequence (P41274) of human CD137L, the amino acid sequence (P43489) of human OX40, the amino acid sequence (Q9Y5U5) of human GITR, the amino acid sequence (P26842) of human CD27 were obtained according to the information of the Uniprot™ protein database; the corresponding encoding DNA sequences were designed by using DNAworks™ online tool to obtain the above sequences and the genes of EGFP fusion proteins, including the genes of hCD137-EGFP, hCD137L-EGFP, mCD137-EGFP, hOX40-EGFP, hCD27-EGFP and hGITR-EGFP. Their DNA fragments were obtained by artificial synthesis. The synthesized gene sequences were double-digested with HindIII and EcoRI (Fermentas) respectively, and subcloned into the commercial vector pcDNA4/myc-HisA (Invitrogen, V863-20), and the accuracy of the constructed plasmids were verified by sequencing. The recombinant plasmid DNAs were obtained: pcDNA4-hCD137-hFc, pcDNA4-hCD137-muFc, pcDNA4-RhCD137-muFc, pcDNA4-hOX40-EGFP, pcDNA4-hCD137-EGFP, pcDNA4-mCD137-EGFP, pcDNA4-hCD137L-EGFP, pcDNA4-hCD27-EGFP and pcDNA4-hGITR-EGFP.

The above EGFP recombinant plasmids were transfected into HEK293 (ATCC, CRL-1573™) cells, and the expressions of hOX40, hCD137, mCD137, and hCD27 were confirmed by the fluorescence activated signal sorting (FACS) at 48 h after transfection.

pcDNA4-hCD137-Fc, pcDNA4-hCD137-muFc and pcDNA4-RhCD137-muFc were transiently transfected into HEK293 cells for protein production. The recombinant expression plasmids were diluted with a FreeStyle293 medium and PEI (polyethylenimine) solution for transformation was added; each group of plasmid/PEI mixture was added into the cell suspension respectively and incubated at 37° C., 10% CO2 and 90 rpm; after 5-6 days, the transiently expressed culture supernatant was collected and purified by Protein A™ affinity chromatography to obtain hCD137-Fc, hCD137-muFc and RhCD137-muFc protein samples for the following examples. The obtained protein samples were subjected to preliminary detection by SDS-PAGE, and the target band can be seen clearly.

Example 2. Screening, Cloning, Expressing and Identification of Anti-hCD137 Antibody from Yeast Display Library Yeast display technology was used to screen for complete human antibodies against human CD137. The scFV yeast display library was constructed by cloning the VH and VL genes of the IgM and IgG cDNA from PBMCs of 150 healthy human beings (the linker sequence between the VH and the VL is GGGGSGGGGSGGGGS linker peptide (SEQ ID NO: 1)), with a library volume of 5×10$^8$. The 10-fold volume of yeast library was resuscitated to induce the expression of the antibody on yeast surface; the yeasts were enriched twice with 100 nM biotinylated hCD137-Fc antigens by magnetic bead sorting, and then further enriched twice with biotinylated hCD137 by flow sorting. The enriched yeasts were plated, and monoclones were picked. After amplification and induction of expression, the monoclonal yeasts were analyzed by staining with biotinylated hCD137 or the control antigen hOX40, and the yeast with antigen positive/control yeast negative was regarded as a positive yeast.

The yeast clones confirmed by FACS were subjected to yeast colony PCR and sequencing. The PCR primers were: sequence-F: CGTAGAATCGAGACCGAGGAGA (SEQ ID NO.2); sequence-R: CTGGTGGTGGTGGTTCTGCTAGC (SEQ ID NO.3)); sequencing primers were sequence-R. After sequencing, the results were compared and analyzed using BioEdit™ software.

The gene of the single-chain antibody scFv obtained above was fused with the above human IgG1-Fc gene, and then double-digested with HindIII and EcoRI (Fermentas™) and cloned into the commercial vector pcDNA4/myc-HisA. The cloning and extraction in small amount of the plasmid were carried out according to the standard operation of Molecular Cloning™. The extracted plasmid was transiently expressed in HEK 293 cells and purified through a Protein A column.

The hCD137-EGFP cells were resuspended in 0.5% PBS-BSA Buffer, and 2 µg of the above purified anti-hCD137 scFv antibody was added, and the relevant control was set at the same time. The negative control was 2 µg of hIgG 1 protein. The secondary antibody was anti-hIg-PE. After staining, it was detected by flow cytometry. In this way, antibodies that bind to the hCD137 antigen on cell surface were identified.

After screening and identification, two antibodies with better properties were obtained: C2scFv and C14scFv. As shown in FIG. 1, the two anti-hCD137 antibodies were able to bind to the hCD137 on cell surface, whereas the negative control was unable to bind to the hCD137 on cell surface.

The amino acid sequence of heavy chain variable region of C2 scFv is:

```
                                           (SEQ ID NO. 4)
EVQLVESGGGLVQPGGSLRLSCAASGFTVSDYYMNWIRQAPGKGLEWVSY

ISSSASGSTIYYADSVKGRFTISRDNANNSLYLHMDSLRAEDTAIYFCAR

VVPAGSGWRWFDPWGQGTLVTVSS
```

The amino acids corresponding to the underlined parts are CDR1 (SEQ ID NO.5), CDR2 (SEQ ID NO.6), and CDR3 (SEQ ID NO.7), respectively.

The corresponding nucleic acid sequence thereof is:

```
                                           (SEQ ID NO. 8)
GAGGTGCAGCTGGTGGAGTCTGGGGGAGGCTTGGTACAGCCTGGAGGGTC

CCTGAGACTCTCCTGTGCAGCCTCTGGATTCACCGTCAGTGACTACTACA

TGAACTGGATCCGCCAGGCTCCAGGGAAGGGCCTGGAGTGGGTTTCATAC

ATTAGTAGTAGTGCTAGTGGTAGTACCATATACTACGCAGACTCTGTGAA

GGGCCGATTCACCATCTCCAGGGACAACGCCAACAACTCACTGTATCTGC
```

ACATGGACAGCCTGAGAGCCGAGGACACGGCCATATACTTCTGTGCGAGA

GTCGTCCCAGCTGGAAGTGGGTGGAGGTGGTTCGACCCCTGGGGCCAGGG

TACCCTGGTCACTGTCTCCTCA

The amino acid sequence of light chain variable region of C2 scFv is:

(SEQ ID NO. 9)
QSVLIQPPSASGSPGQSVTISC<u>TGISSDVGAYDYVS</u>WYQQHPGKVPKLMI

Y<u>EVSKRPS</u>GVPDRFSGSKSGDTASLTVSGLQAEDEADYYC<u>SSHAGSNNFY</u>

VFGTGTKLTVL

The amino acids corresponding to the underlined parts are CDR1 (SEQ ID NO.10), CDR2 (SEQ ID NO.11), and CDR3 (SEQ ID NO.12), respectively.

Its corresponding nucleic acid sequence is:

(SEQ ID NO. 13)
CAGTCTGTTCTGATTCAGCCTCCCTCCGCGTCCGGGTCTCCTGGACAGTC

AGTCACCATCTCCTGCACTGGAATCAGCAGTGACGTTGGTGCTTATGACT

ATGTCTCCTGGTACCAACAGCACCCAGGCAAAGTCCCCAAACTCATGATT

TATGAGGTCAGTAAGCGGCCCTCAGGGGTCCCTGATCGCTTCTCTGGCTC

CAAGTCTGGCGACACGGCCTCCCTGACCGTCTCTGGGCTCCAGGCTGAGG

ATGAGGCTGATTACTACTGCAGCTCACATGCAGGCAGCAACAATTTTTAT

GTCTTCGGAACTGGGACCAAGCTGACCGTCCTA

The amino acid sequence of heavy chain variable region of C14 scFv is:

(SEQ ID NO. 14)
QVQLQQSGPGLVKPSQTLSLTCAISGDSVS<u>SNSAAWN</u>WIRQSPSRGLEW

LG<u>RTYYRSKWYNDYAPSVES</u>RITINPDTSKNQFSLQLSSVTPEDTAVYY

CARD<u>PPYVLSTFDI</u>WGQGTMVTVSS

The amino acids corresponding to the underlined parts are CDR1 (SEQ ID NO.15), CDR2 (SEQ ID NO.16), and CDR3 (SEQ ID NO.17), respectively.

Its corresponding nucleic acid sequence is:

(SEQ ID NO. 18)
CAGGTACAGCTGCAGCAGTCAGGTCCAGGACTGGTGAAGCCCTCGCAGAC

CCTCTCACTCACCTGTGCCATCTCCGGGGACAGTGTTTCTAGCAACAGTG

CTGCTTGGAACTGGATCAGGCAGTCCCCATCGAGGGGCCTTGAGTGGCTG

GGAAGGACATACTACAGGTCCAAGTGGTATAATGATTATGCACCATCTGT

GGAAAGTCGAATAACCATCAACCCAGACACATCCAAGAACCAGTTCTCCC

TGCAGCTGAGCTCTGTGACTCCCGAGGACACGGCTGTGTACTACTGTGCA

AGAGACCCTCCTTATGTGCTCAGTACTTTTGATATCTGGGGCCAAGGGAC

AATGGTCACCGTCTCCTCA

The amino acid sequence of light chain variable region of C14 scFv is:

(SEQ ID NO. 19)
NFMLTQPPSVSESPGKTVTISC<u>TRSSGNIASFYVQ</u>WFQQRPGSSPTTVIY

<u>EDDQRPS</u>GVPDRFSGSIDRSSNSASLTISGLTTDDEADYYC<u>QSYDTNNVI</u>

FGGGTKLTVL

The amino acids corresponding to the underlined parts are CDR1 (SEQ ID NO.20), CDR2 (SEQ ID NO.21), and CDR3 (SEQ ID NO.22), respectively.

Its corresponding nucleic acid sequence is:

(SEQ ID NO. 23)
AATTTTATGCTGACTCAGCCCCCCTCTGTGTCGGAGTCCCCGGGGAAGAC

GGTAACCATCTCCTGCACCCGCAGCAGTGGGAACATTGCCAGCTTCTATG

TGCAGTGGTTTCAACAGCGCCCGGGCAGTTCCCCCACCACTGTGATCTAT

GAAGATGACCAAAGACCCTCTGGGGTCCCTGATCGGTTCTCTGGCTCCAT

CGACAGATCGTCCAACTCTGCCTCCCTCACCATTTCTGGACTGACGACTG

ACGACGAGGCTGACTACTACTGTCAGTCTTATGATACCAACAATGTCATA

TTCGGCGGAGGGACCAAGCTGACCGTCCTA

Example 3. Identification of Anti-hCD137 scFv Characteristics 3.1 Identification of Specific Binding to hCD137 (FACS):

HEK293 cells expressing hCD137-EGFP, hOX40-EGFP, hCD27-EGFP and hGITR-EGFP constructed in Example 1 were resuspended in 0.5% PBS-BSA Buffer and anti-hCD137 C2scFv and C14 scFv protein were added, the negative control was hIgG Fc protein, then the mixture was incubated on ice for 20 min. After washing, secondary antibody anti-hIg-PE (eBioscience™) was added and was incubated on ice for 20 min. After washing, the cells were resuspended in 500 μL of 0.5% PBS-BSA Buffer and detected by flow cytometry. As shown in FIG. 2, anti-hCD137 C2scFv and C14 scFv were both able to bind to hCD137-EGFP cells, but unable to bind to several other EGFP cells (hOX40-EGFP-293F, hCD27-EGFP-293F and hGITR-EGFP-293F), showing good capability of specificity.

Figure 3:
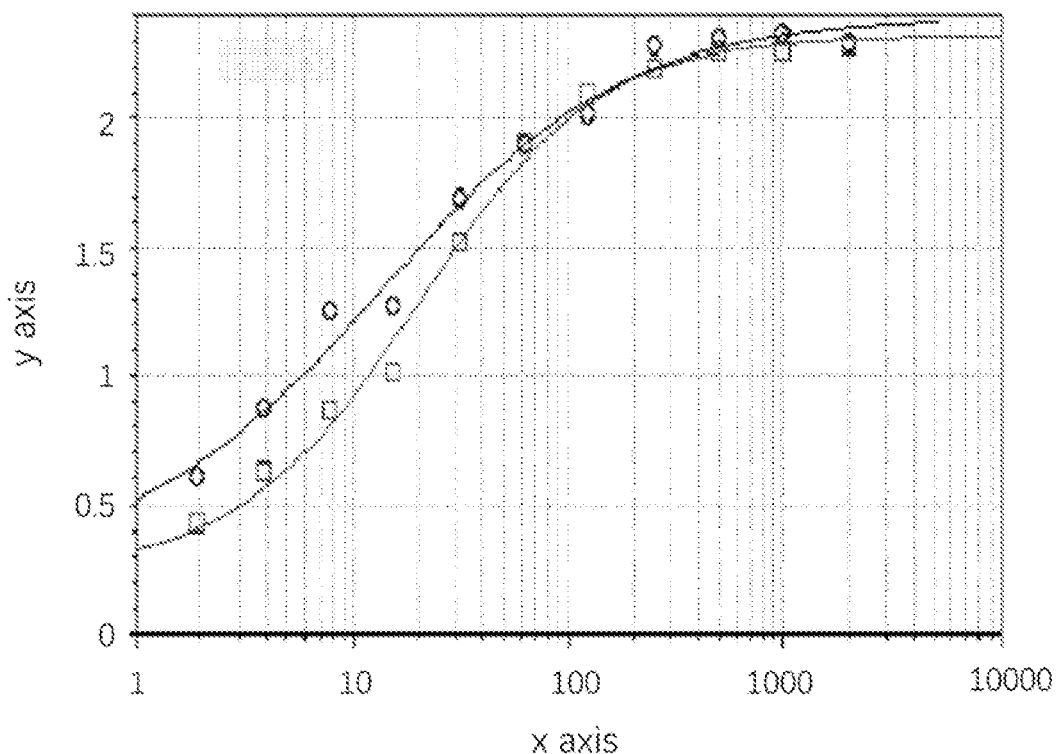
FIG. 3 is a graph showing the detection of the binding capacity of anti-CD137 scFv to hCD137 protein.
Figure 4A:
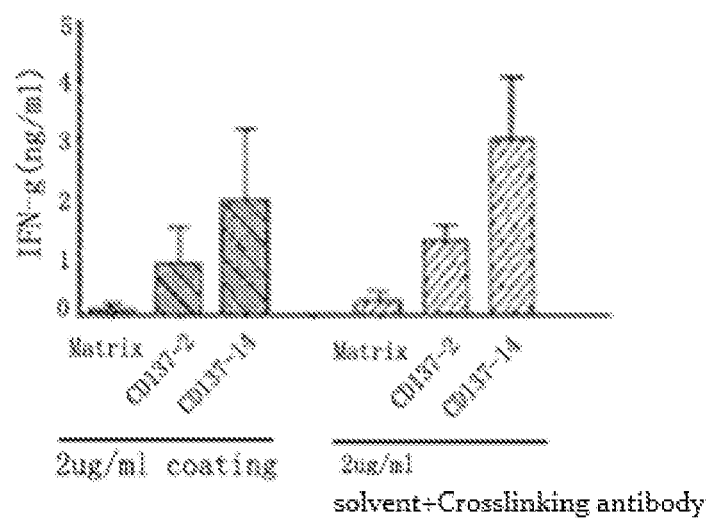
FIG. 4 shows the measurement results of the activities of C2 scFv and C14 scFv agonists.
Figure 4B:
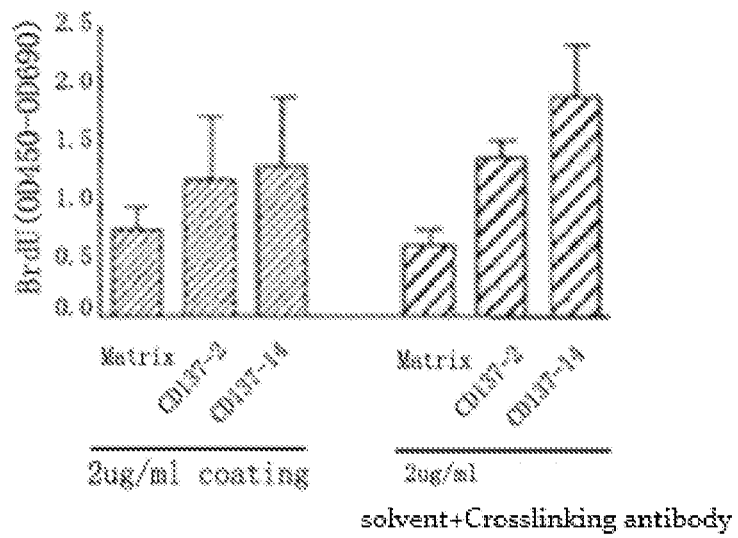
Figure 4C:
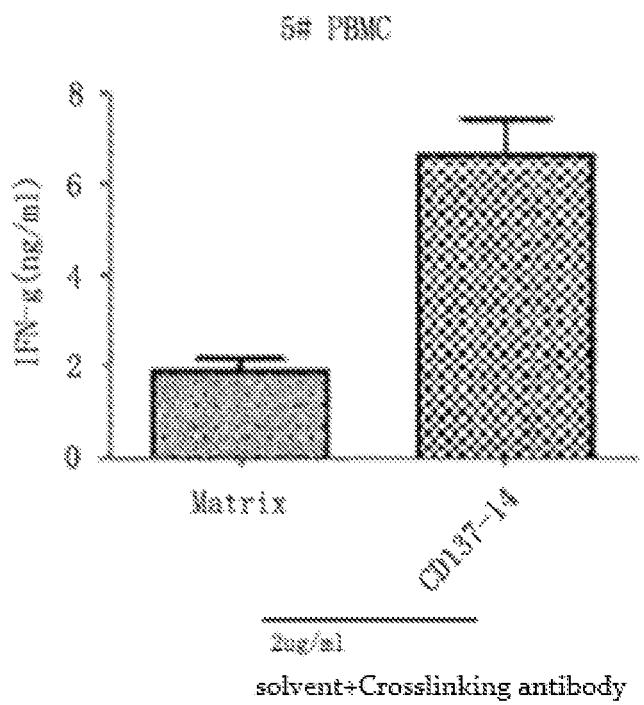
Figure 4D:
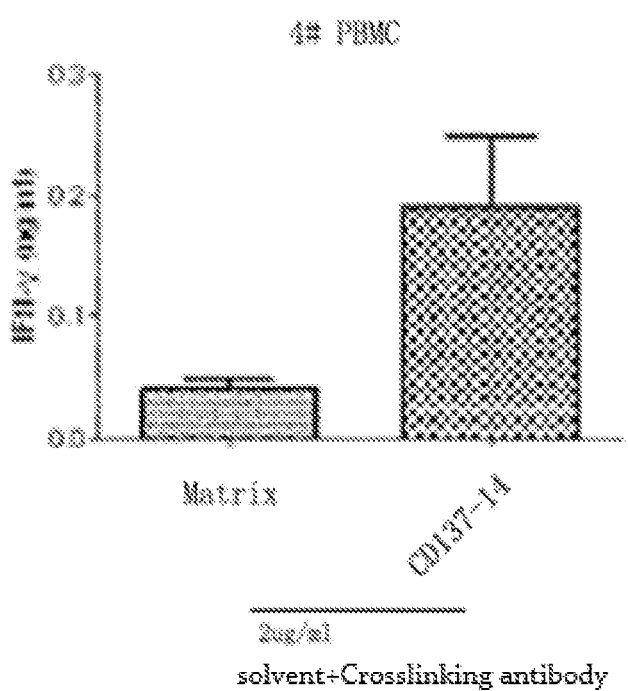

3.2 Detection on the Capacity of Binding to hCD137 Proteins (ELISA):

hCD137-muFc was diluted to 2 μg/mL, 100 μL/well with coating buffer (50 mM $Na_2CO_3$, $NaHCO_3$ pH 9.6), and then stands overnight at 4° C. After washing, the plates were blocked with 3% BSA-PBS for 1 h at 37° C. C2 scFv and C14 scFv antibodies were respectively diluted from 2000 ng/mL and were diluted 2-fold to a total of 11 concentrations, with the diluent (1% BSA-PBS) as a control, and incubated at 37° C. for 2h. Goat anti-hIgG-HRP (Goat anti-hIgG-HRP-conjugated) was added and incubated at 37° C. for 1 h. The soluble one-component TMB™ substrate developing solution was added, and the developing was performed in dark at room temperature for 5-10 min. 2N $H_2SO_4$ 50 μL/well was added to terminate the color development reaction. The $OD_{450\ nm\text{-}650\ nm}$ values were read on MD SpectraMax Plus 384 microplate Reader™, and SoftMax Pro v5.4™ was used for data processing and diagraph analysis, with the results shown in FIG. 3.

3.3 Detection on the Capacity of Binding to hCD137 Proteins (SPR Process):

The binding kinetics of anti-hCD137 C2scFv and C14 scFv antibodies against the recombinant human CD137 were measured by surface plasmon resonance (SPR) process using a BIAcore X100™ instrument. Anti-hFc antibody (not cross-identifying mouse Fc) was conjugated on CM5 chip, C2 scFv or C14 scFv was diluted to 5 nM with running buffer and captured as a ligand by the antibody on the chip. CD137-muFc was diluted with running buffer to 1000-31.6 nM, diluted twice to a total of 6 concentrations. The injection time was 180 s, the dissociation time was 1800 s and the regeneration time was 60 s. The running buffer was HBS-EP+, and the regeneration buffer was 10 mM glycine-HCl (pH 2.0). The association rate ($K_{on}$) and the dissociation rate ($K_{off}$) were calculated using a simple one-to-one Languir™ binding model (BIAcore Evaluation Software version 3.2™). The equilibrium dissociation constant ($K_D$) was calculated as the ratio of $K_{off}/K_{on}$.

The measured binding affinities of anti-hCD137 antibodies were seen in Table 1.

TABLE 1

Detection of binding kinetics between anti-hCD137 antibody and hCD137

| Name | $K_{on}$ (1/Ms) | $K_{off}$ (1/s) | $K_D$ (M) |
| --- | --- | --- | --- |
| C2ScFv | 1.103E+4 | 1.281E-4 | 1.161E-8 |
| C14 ScFv | 1.117E+4 | 2.634E-4 | 2.380E-8 |

Example 4. Determination on the Activities of Anti-CD137 C2 scFv and C14 scFv Agonists Peripheral blood mononuclear cells (PBMCs) were isolated from peripheral blood concentrated leukocytes of healthy donors by the density gradient centrifugation using human lymphocyte separation fluid (Tianjin Hao Yang™) and seeded into RPMI™ complete medium. 96-well plates were pre-coated with 50 µL of 1 µg/mL anti-CD3 overnight at 4° C. Experimental groups were coated with 50 µL of 2 µg/mL C2 scFv or C14 scFv for 2 h at 37° C., and meanwhile, soluble C2 scFv or C14 scFv with a final concentration of 2 µg/mL and cross-link (Jackson ImmunoResearch Laboratories: 109-006-008™) with a final concentration of 2 µg/mL were added. The negative control was RPMI™ complete medium. The amount of PBMCs was 2×10⁵/well, the cells were cultured for five days and then the supernatant was taken. As shown in FIG. 4, the level of IFN-γ in the supernatant was detected by the IFN-γ ELISA™ into RPMI™ detection kit (Eioscience™) and the proliferation of T cells was detected by the BrdU™ staining kit (Roche: 11647229001). It can be seen that C2 scFv and C14 scFv have good activity in activating PBMCs and promoting the proliferation of T cells under both coating administration mode and cross-link administration mode, while the agonist activity of C14 scFv is slightly stronger than that of C2 scFv.

Peripheral blood mononuclear cells (PBMCs) were isolated from peripheral blood concentrated leukocytes of healthy donors (4# and 5#) by the density gradient centrifugation using human lymphocyte separation fluid (Tianjin Hao Yang™) and seeded into RPMI™ complete medium. 96-well plates were pre-coated with 50 µL of 1 µg/mL anti-CD3 overnight at 4° C. Experimental groups were coated with 50 µL of 2 µg/mL C14 scFv and cross-link (Jackson ImmunoResearch Laboratories: 109-006-008™) with a final concentration of 2 µg/mL. The negative control was RPMI™ complete medium. The amount of PBMCs was 2×10⁵/well, the cells were cultured for five days and then the supernatant was taken. As shown in FIG. 4, the level of IFN-γ in the supernatant of 5# PBMC (FIG. 4) and the level of IFN-γ in the supernatant of 4# PBMC (FIG. 4) were detected by the IFN-γ ELISA™ detection kit (eioscience™), it can be seen that C14 scFv could increase the level of the activated PBMC secreting IFN-γ.

Example 5. Antibody In Vitro Affinity Maturation

5.1 Construction of the Yeast Expression Library with Improved Affinity

The standard PCR reaction was performed using the pcDNA4-CD137-14-Fc plasmid constructed in Embodiment 2 as a template, pcDNA4-F: TCTGGTGGTGGTGGTTCTGCTAGC (SEQ ID NO.24) and cMyc-BBXhoI: GCCAGATCTCGAGCTATTACAAGTCTTCTTCAGA AATAAGCTTTTGTTCTAGAATTCC G (SEQ ID NO.25) as primers. The resulting PCR products were digested with NheI and BglII (Fermentas™) to construct a recombinant plasmid. Next, a random mutation PCR product of scFv was obtained by error prone PCR with reference to the method of Ginger et al. (2006) NatProtocl (2): 755-68. The primers used were ep-F: TAATACGACTCACTATAGGG (SEQ ID NO.26) and ep-R: GGCAGCCCCATAAACACACAGTAT (SEQ ID NO.27). The resulting PCR products were purified by the GeneJET DNA purification Kit™ from Fermentas and then precipitated in ethanol to a concentration greater than 1 µg/µL. The remaining operation steps refer to the method of Ginger et al. (2006) Nat Protocl (2): 755-68 to obtain a yeast library with mature affinities by virtue of yeast electrical conversion and in vivo recombination method.

5.2 Screening of Anti-CD137 C14# scFv of Yeasts with Improved Affinity

Figure 5A:
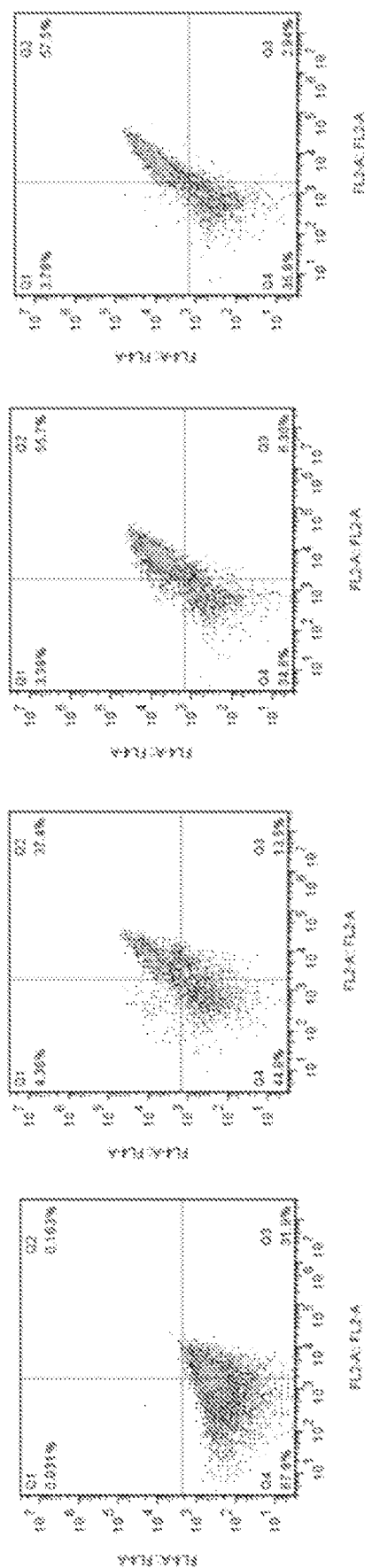
FIG. 5S shows the yeast staining results by CD137 protein after affinity maturation.
Figure 5B:
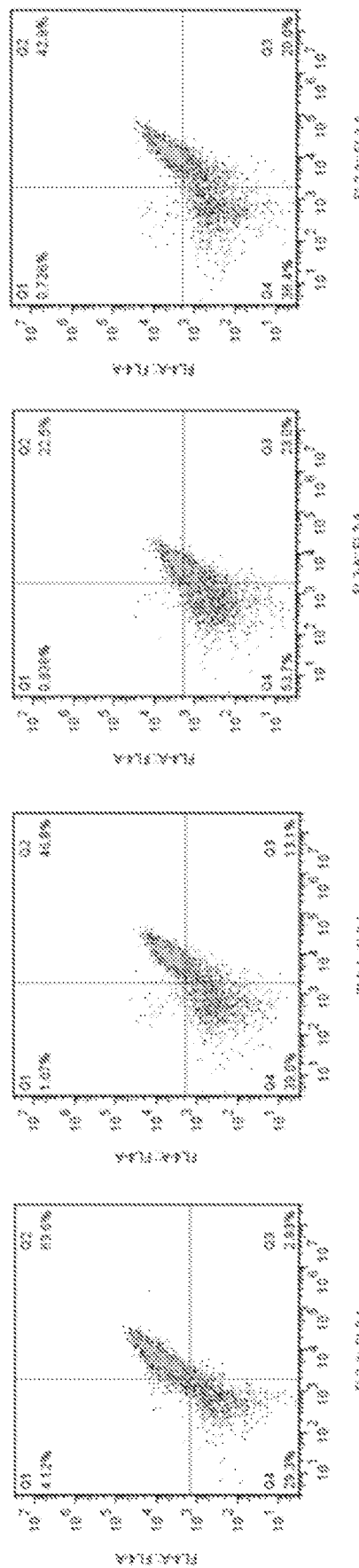
Figure 6A:
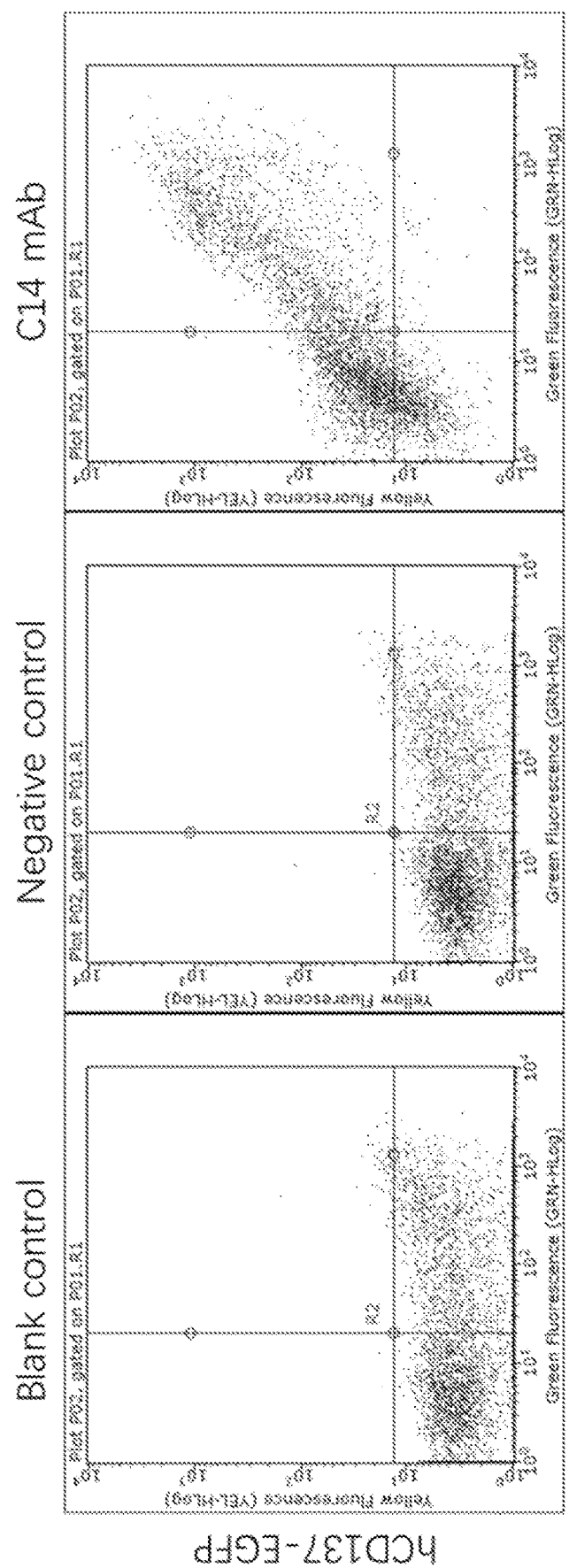
FIG. 6 is a graph showing the results of purified anti-hCD137 C14# mAb specifically binding to hCD137-EGFP cells, where X-axis represents the fluorescence intensity of EGFP, and Y-axis represents the fluorescence intensity of anti-hIg-PE.
Figure 6B:
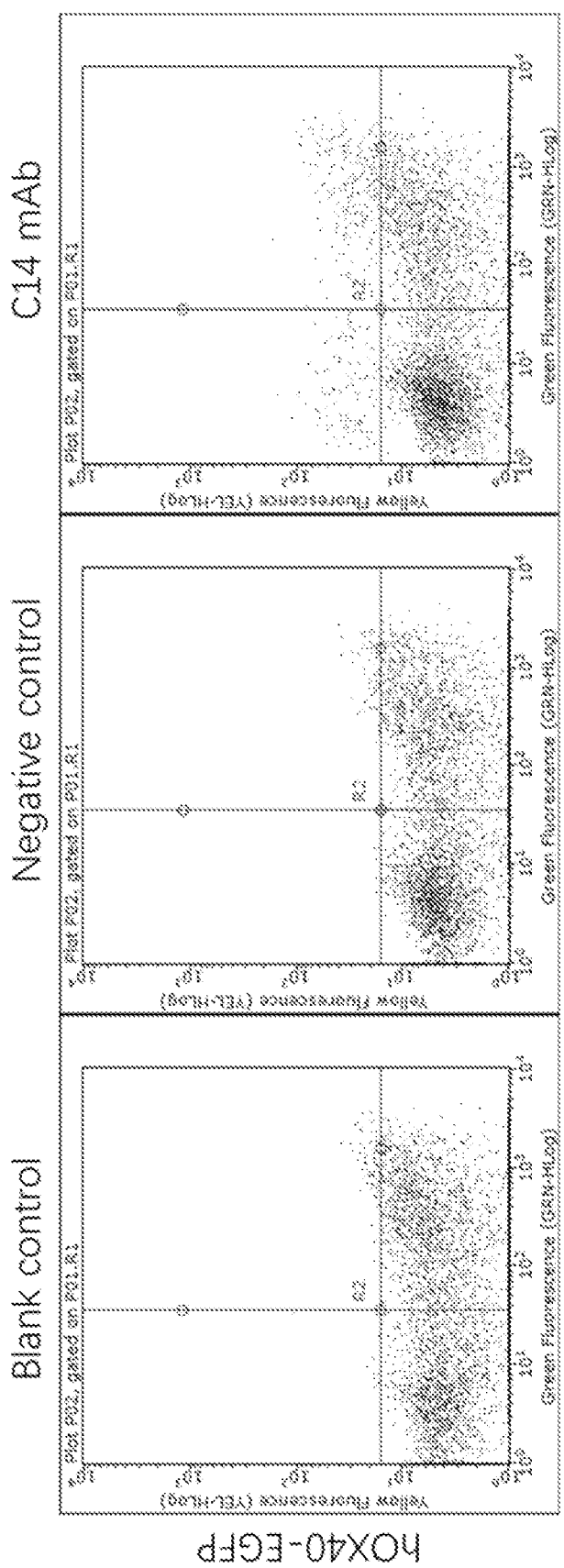
Figure 6C:
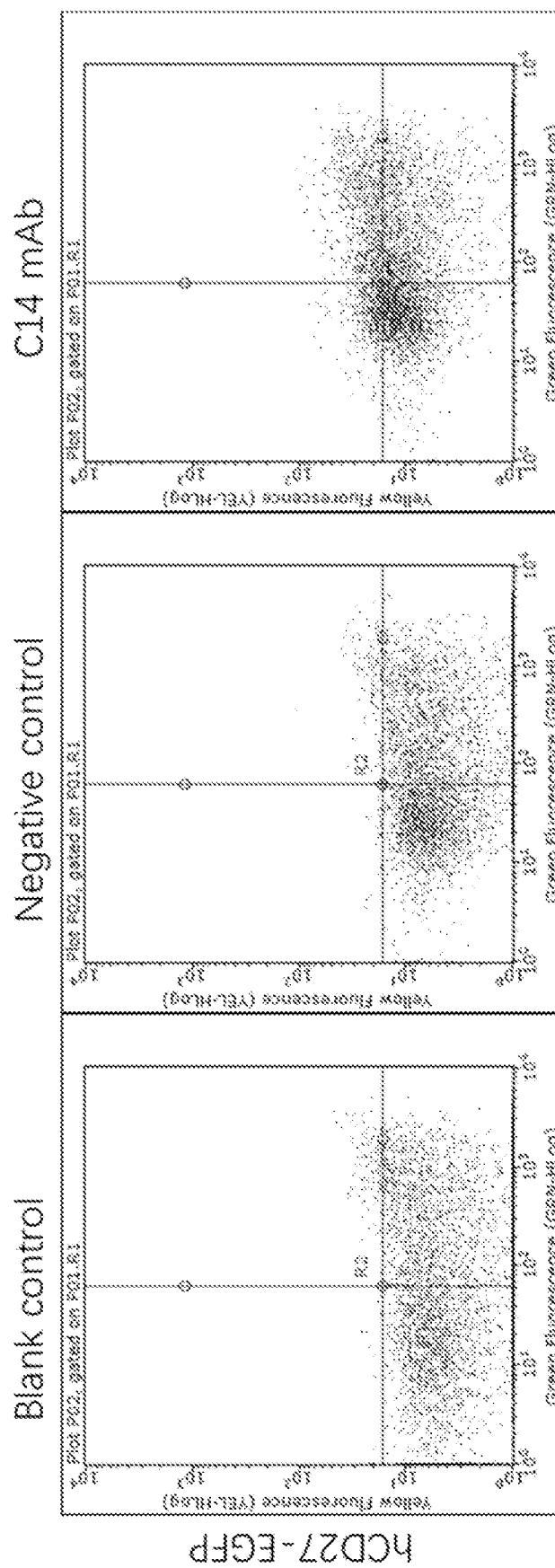
Figure 6D:
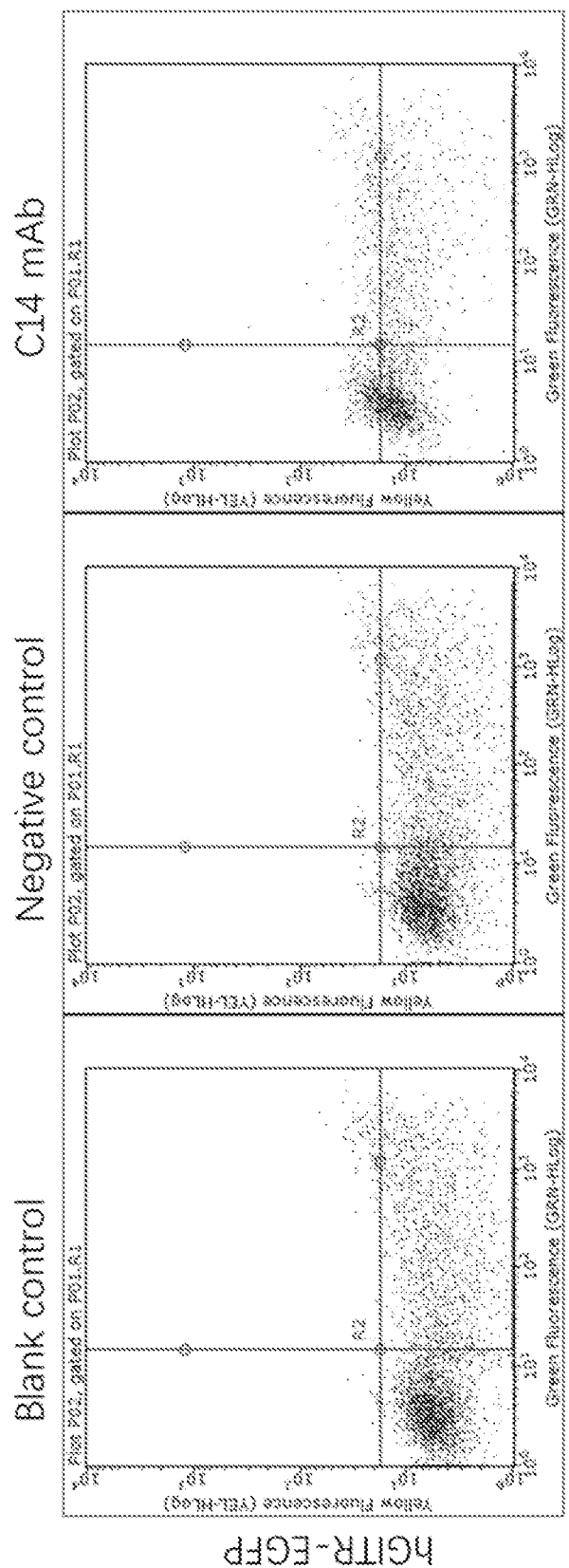

The affinity-matured yeast library obtained above was subjected to two rounds of fluorescence-activated cell sorting with 10 nM and 1 nM hCD137-Fc protein, and the resulting yeast products were plated and subjected to monoclonal identification. Using the method of staining with a low concentration of antigen, with the previously obtained wild-type yeast as a control, the yeast monoclones with improved affinity were identified by flow staining, with the results of yeast staining shown in FIG. 5.

The yeast clones confirmed by FACS were subjected to yeast colony PCR and sequencing, the method as above. The results of sequence analysis were shown in the following table:

TABLE 2

Results of sequence analysis of yeast monoclones with improved affinity

| Name | Mutation Site |
| --- | --- |
| CD137-14-1 | Position H5: Q mutated to P; Position L93: T mutated to I; Position L95: N mutated to S |
| CD137-14-2 | Position L95: N mutated to K |
| CD137-14-3 | Position L50: E mutated to D |
| CD137-14-4 | Position H43: R mutated to G; Position H54: K mutated to R; Position L2: F mutated to S; Position L15: P mutated to S |

TABLE 2-continued

Results of sequence analysis of yeast monoclones with improved affinity

| Name | Mutation Site |
| --- | --- |
| CD137-14-10 | Position H61: P mutated to S; Position L2: F mutated to S |
| CD137-14-13 | Position H57: N mutated to S; Position H65: S mutated to G |
| CD137-14-14 | Position H32: N mutated to D; Position L95: N mutated to K | kit (PL14) supplied by AidLab™. The recombinant constructed light chain and the heavy chain plasmids were co-transfected into HEK293 cells to carry out the antibody expression, transiently cultured for 5-6 days, and then the culturing supernatant was collected, and purified through a Protein A™ affinity chromatography method to obtain an anti-hCD137 antibody: C14mAb.

The scFv-type antibody with matured affinity was formatted into an IgG-type antibody according to the same method, and a series of anti-CD137 14# mAb variants were obtained, as shown in the following table.

| Name | Sequence Information |
| --- | --- |
| anti-CD137 14#H54H57 mAb | Light chain sequence unchanged; Heavy chain H54 Position: K mutated to R; H57 Position: N mutated to S; H61 Position: P mutated to S |
| anti-CD137 14#H32 mAb | Light chain sequence unchanged; Heavy chain H32 Position: N mutated to D |
| anti-CD137 14#L50 mAb | Heavy chain sequence unchanged; Light chain L50 Position: E mutated to D |
| anti-CD137 14#L95mAb | Heavy chain sequence unchanged; Light chain L95 Position: N mutated to K |
| anti-CD137 14#L93L95mAb | Heavy chain sequence unchanged; Light chain L95 Position: N mutated to K; L93 Position: T mutated to I |
| anti-CD137 14#mAb new | Heavy chain sequence unchanged; Light chain L95 Position: N mutated to K; L50 Position: E mutated to D; L93 Position: T mutated to I |

Example 6. scFv-Type Antibody Formatted to IgG-Type Antibody

The amino acid sequence of the human IgG4 constant region was obtained based on the amino acid sequence (P01861) of the constant region of the human immunoglobulin gamma(γ)4 (IgG4) in the Uniprot™ protein database. The corresponding encoding DNA sequence was designed by using DNAworks™ online tool to obtain the gene of the human IgG4 constant region. The VH sequence of the C14 heavy chain variable region obtained through screening was spliced with the gene sequence of the human IgG4 constant region, and the spliced genes were synthesized, and double-digested with HindIII and EcoRI (Fermentas™) and subcloned into the vetor pcDNA4/myc-HisA, to obtain pcDNA4-C14HC.

The amino acid sequence of the human lambda light chain constant region was obtained based on the amino acid sequence (AOM8Q6) of the constant region of the human immunoglobulin lambda (λ) in the Uniprot™ protein database. The corresponding encoding DNA sequence was designed by using DNAworks™ online tool to obtain the gene of the human lambda (λ) light chain constant region. The VL sequence of the C14 light chain variable region obtained through screening was spliced with the gene sequence of the human lambda (λ) light chain constant region, and the spliced genes were synthesized, and double-digested with HindIII and EcoRI (Fermentas™) and subcloned into the vetor pcDNA4/myc-HisA, to obtain pcDNA-C14LC.

Plasmid extraction of the heavy and light chain plasmids obtained above was carried out using the plasmid extraction Their sequences were shown as below:

The amino acid sequence of heavy chain variable region of anti-CD137 14# H54H57 mAb is:

(SEQ ID NO. 28)
QVQLQQSGPGLVKPSQTLSLTCAISGDSVSSNSAAWNWIRQSPSRGLEWLG

RTYYRSRWYSDYASSVESRITINPDTSKNQFSLQLSSVTPEDTAVYYCARD

PPYVLSTFDIWGQGTMVTVSS

The amino acids in frame were mutation sites, the amino acids corresponding to the underlined parts are CDR1 (SEQ ID NO.15), CDR2 (SEQ ID NO.29), and CDR3 (SEQ ID NO.17), respectively.

The corresponding nucleic acid sequence thereof is:

(SEQ ID NO. 30)
CAGGTACAGCTGCAGCAGTCAGGTCCAGGACTGGTGAAGCCCTCGCAGACC

CTCTCACTCACCTGTGCCATCTCCGGGGACAGTGTTTCTAGCAACAGTGCT

GCTTGGAACTGGATCAGGCAGTCCCCATCGAGGGGCCTTGAGTGGCTGGGA

AGGACATACTACAGGTCCAGGTGGTATAGTGATTATGCATCATCTGTGGAA

AGTCGAATAACCATCAACCCAGACACATCCAAGAACCAGTTCTCCCTGCAG

CTGAGCTCTGTGACTCCCGAGGACACGGCTGTGTACTACTGTGCAAGAGAC

CCTCCTTATGTGCTCAGTACTTTTGATATCTGGGGCCAAGGGACAATGGTC

ACCGTCTCCTCA

The amino acid sequence of light chain variable region of anti-CD137 14# H54H57 mAb is:

(SEQ ID NO. 19)
NFMLTQPPSVSESPGKTVTISCTRSSGNIASFYVQWFQQRPGSSPTTVIY

EDDQRPSGVPDRFSGSIDRSSNSASLTISGLTTDDEADYYCQSYDTNNVI

FGGGTKLTVL

The amino acids corresponding to the underlined parts are CDR1 (SEQ ID NO.20), CDR2 (SEQ ID NO.21), and CDR3 (SEQ ID NO.22), respectively.

The corresponding nucleic acid sequence thereof is:

(SEQ ID NO. 23)
AATTTTATGCTGACTCAGCCCCCCTCTGTGTCGGAGTCCCCGGGGAAGAC

GGTAACCATCTCCTGCACCCGCAGCAGTGGGAACATTGCCAGCTTCTATG

TGCAGTGGTTTCAACAGCGCCCGGGCAGTTCCCCCACCACTGTGATCTAT

GAAGATGACCAAAGACCCTCTGGGGTCCCTGATCGGTTCTCTGGCTCCAT

CGACAGATCGTCCAACTCTGCCTCCCTCACCATTTCTGGACTGACGACTG

ACGACGAGGCTGACTACTACTGTCAGTCTTATGATACCAACAATGTCATA

TTCGGCGGAGGGACCAAGCTGACCGTCCTA

The amino acid sequence of heavy chain variable region of anti-CD137 14# H32 mAb is:

(SEQ ID NO. 31)
QVQLQQSGPGLVIUSQTLSLTCAISGDSVSSDSAAWNWIRQSPSRGLEWLG

RTYYRSKWYNDYAPSVESRITINPDTSKNQFSLQLSSVTPEDTAVYYCARD

PPYVLSTFDIWGQGTMVTVSS

The amino acids in frame were mutation sites, the amino acids corresponding to the underlined parts are CDR1 (SEQ ID NO.32), CDR2 (SEQ ID NO.16), CDR3 (SEQ ID NO.17), respectively.

The corresponding nucleic acid sequence thereof is:

(SEQ ID NO. 33)
CAGGTACAGCTGCAGCAGTCAGGTCCAGGACTGGTGAAGCCCTCGCAGACC

CTCTCACTCACCTGTGCCATCTCCGGGGACAGTGTTTCTAGCGACAGTGCT

GCTTGGAACTGGATCAGGCAGTCCCCATCGAGGGGCCTTGAGTGGCTGGGA

AGGACATACTACAGGTCCAAGTGGTATAATGATTATGCACCATCTGTGGAA

AGTCGAATAACCATCAACCCAGACACATCCAAGAACCAGTTCTCCCTGCAG

CTGAGCTCTGTGACTCCCGAGGACACGGCTGTGTACTACTGTGCAAGAGAC

CCTCCTTATGTGCTCAGTACTTTTGATATCTGGGGCAAGGGACAATGGTC

ACCGTCTCCTCA

The amino acid sequence of anti-CD137 14# H32 mAb light chain variable region is:

(SEQ ID NO. 19)
NFMLTQPPSVSESPGKTVTISCTRSSGNIASFYVQWFQQRPGSSPTTVIY

EDDQRPSGVPDRFSGSIDRSSNSASLTISGLTTDDEADYYCQSYDTNNVI

FGGGTKLTVL

The amino acids corresponding to the underlined parts are CDR1 (SEQ ID NO.20), CDR2 (SEQ ID NO.21), and CDR3 (SEQ ID NO.22), respectively.

The corresponding nucleic acid sequence thereof is:

(SEQ ID NO. 23)
AATTTTATGCTGACTCAGCCCCCCTCTGTGTCGGAGTCCCCGGGGAAGAC

GGTAACCATCTCCTGCACCCGCAGCAGTGGGAACATTGCCAGCTTCTATG

TGCAGTGGTTTCAACAGCGCCCGGGCAGTTCCCCCACCACTGTGATCTAT

GAAGATGACCAAAGACCCTCTGGGGTCCCTGATCGGTTCTCTGGCTCCAT

CGACAGATCGTCCAACTCTGCCTCCCTCACCATTTCTGGACTGACGACTG

ACGACGAGGCTGACTACTACTGTCAGTCTTATGATACCAACAATGTCATA

TTCGGCGGAGGGACCAAGCTGACCGTCCTA

The amino acid sequence of heavy chain variable region of anti-CD137 14# L50 mAb is:

(SEQ ID NO. 14)
QVQLQQSGPGLVKPSQTLSLTCAISGDSVSSNSAAWNWIRQSPSRGLEWL

GRTYYRSKWYNDYAPSVESRITINPDTSKNQFSLQLSSVTPEDTAVYYCA

RDPPYVLSTFDIWGQGTMVTVSS

The amino acids corresponding to the underlined parts are CDR1 (SEQ ID NO.15), CDR2 (SEQ ID NO.16), and CDR3 (SEQ ID NO.17), respectively.

Its corresponding nucleic acid sequence is:

(SEQ ID NO. 18)
CAGGTACAGCTGCAGCAGTCAGGTCCAGGACTGGTGAAGCCCTCGCAGAC

CCTCTCACTCACCTGTGCCATCTCCGGGGACAGTGTTTCTAGCAACAGTG

CTGCTTGGAACTGGATCAGGCAGTCCCCATCGAGGGGCCTTGAGTGGCTG

GGAAGGACATACTACAGGTCCAAGTGGTATAATGATTATGCACCATCTGT

GGAAAGTCGAATAACCATCAACCCAGACACATCCAAGAACCAGTTCTCCC

TGCAGCTGAGCTCTGTGACTCCCGAGGACACGGCTGTGTACTACTGTGCA

AGAGACCCTCCTTATGTGCTCAGTACTTTTGATATCTGGGGCCAAGGGAC

AATGGTCACCGTCTCCTCA

The amino acid sequence of light chain variable region of anti-CD137 14# L50 mAb is:

(SEQ ID NO. 34)
NFMLTQPPSVSESPGKTVTISCTRSSGNIASFYVQWFQQRPGSSPTTVIYD

DDQRPSGVPDRFSGSIDRSSNSASLTISGLTTDDEADYYCQSYDTNNVIFG

GGTKLTVL

The amino acids in frame were mutation sites, the amino acids corresponding to the underlined parts are CDR1 (SEQ ID NO.20), CDR2 (SEQ ID NO.35), and CDR3 (SEQ ID NO.22), respectively.

The corresponding nucleic acid sequence thereof is:

(SEQ ID NO. 36)
AATTTTATGCTGACTCAGCCCCCCTCTGTGTCGGAGTCCCCGGGGAAGACG

GTAACCATCTCCTGCACCCGCAGCAGTGGGAACATTGCCAGCTTCTATGTG

CAGTGGTTTCAACAGCGCCCGGGCAGTTCCCCCACCACTGTGATCTAT`GAC`

GATGACCAAAGACCCTCTGGGGTCCCTGATCGGTTCTCTGGCTCCATCGAC

AGATCGTCCAACTCTGCCTCCCTCACCATTTCTGGACTGACGACTGACGAC

GAGGCTGACTACTACTGTCAGTCTTATGATACCAACAATGTCATATTCGGC

GGAGGGACCAAGCTGACCGTCCTA

The amino acid sequence of heavy chain variable region of anti-CD137 14# L95mAb is:

(SEQ ID NO. 14)
QVQLQQSGPGLVKPSQTLSLTCAISGDSVS<u>SNSAAWN</u>WIRQSPSRGLEWL

<u>GRTYYRSKWYNDYAPSVES</u>RITINPDTSKNQFSLQLSSVTPEDTAVYYCA

R<u>DPPYVLSTFDI</u>WGQGTMVTVSS

The amino acids corresponding to the underlined parts are CDR1 (SEQ ID NO.15), CDR2 (SEQ ID NO.16), and CDR3 (SEQ ID NO.17), respectively.

The corresponding nucleic acid sequence thereof is:

(SEQ ID NO. 18)
CAGGTACAGCTGCAGCAGTCAGGTCCAGGACTGGTGAAGCCCTCGCAGAC

CCTCTCACTCACCTGTGCCATCTCCGGGGACAGTGTTTCTAGCAACAGTGC

TGCTTGGAACTGGATCAGGCAGTCCCCATCGAGGGGCCTTGAGTGGCTGG

GAAGGACATACTACAGGTCCAAGTGGTATAATGATTATGCACCATCTGTG

GAAAGTCGAATAACCATCAACCCAGACACATCCAAGAACCAGTTCTCCCT

GCAGCTGAGCTCTGTGACTCCCGAGGACACGGCTGTGTACTACTGTGCAA

GAGACCCTCCTTATGTGCTCAGTACTTTTGATATCTGGGGCCAAGGGACA

ATGGTCACCGTCTCCTCA

The amino acid sequence of light chain variable region of anti-CD137 14# L95mAb is:

(SEQ ID NO. 37)
NFMLTQPPSVSESPGKTVTISC<u>TRSSGNIASFYVQ</u>WFQQRPGSSPTTVIYE

<u>DDQRPSGVPDRFSGS</u>IDRSSNSASLTISGLTTDDEADYYC<u>QSYDTN`R`VI</u>FG

GGTKLTVL

The amino acids in frame were mutation sites, the amino acids corresponding to the underlined parts are CDR1 (SEQ ID NO.20), CDR2 (SEQ ID NO.21), and CDR3 (SEQ ID NO.36), respectively.

The corresponding nucleic acid sequence thereof is:

(SEQ ID NO. 39)
AATTTTATGCTGACTCAGCCCCCCTCTGTGTCGGAGTCCCCGGGGAAGACG

GTAACCATCTCCTGCACCCGCAGCAGTGGGAACATTGCCAGCTTCTATGTG

CAGTGGTTTCAACAGCGCCCGGGCAGTTCCCCCACCACTGTGATCTATGAA

GATGACCAAAGACCCTCTGGGGTCCCTGATCGGTTCTCTGGCTCCATCGAC

AGATCGTCCAACTCTGCCTCCCTCACCATTTCTGGACTGACGACTGACGAC

GAGGCTGACTACTACTGTCAGTCTTATGATACCAAC`AAG`GTCATATTCGGC

GGAGGGACCAAGCTGACCGTCCTA

The amino acid sequence of heavy chain variable region of anti-CD137 14# L93L95mAb is:

(SEQ ID NO. 14)
QVQLQQSGPGLVKPSQTLSLTCAISGDSVS<u>SNSAAWN</u>WIRQSPSRGLEWL

<u>GRTYYRSKWYNDYAPSVES</u>RITINPDTSKNQFSLQLSSVTPEDTAVYYCA

R<u>DPPYVLSTFDI</u>WGQGTMVTVSS

The amino acids corresponding to the underlined parts are CDR1 (SEQ ID NO.15), CDR2 (SEQ ID NO.16), and CDR3 (SEQ ID NO.17), respectively.

The corresponding nucleic acid sequence thereof is:

(SEQ ID NO. 18)
CAGGTACAGCTGCAGCAGTCAGGTCCAGGACTGGTGAAGCCCTCGCAGAC

CCTCTCACTCACCTGTGCCATCTCCGGGGACAGTGTTTCTAGCAACAGTG

CTGCTTGGAACTGGATCAGGCAGTCCCCATCGAGGGGCCTTGAGTGGCTG

GGAAGGACATACTACAGGTCCAAGTGGTATAATGATTATGCACCATCTGT

GGAAAGTCGAATAACCATCAACCCAGACACATCCAAGAACCAGTTCTCCC

TGCAGCTGAGCTCTGTGACTCCCGAGGACACGGTCTGTGTACTACTGTGC

AAGAGACCCTCCTTATGTGCTCAGTACTTTTGATATCTGGGGCCAAGGGA

CAATGGTCACCGTCTCCTCA

The amino acid sequence of light chain variable region of anti-CD137 14# L93L95mAb is:

(SEQ ID NO. 40)
NFMLTQPPSVSESPGKTVTISC<u>TRSSGNIASFYVQ</u>WFQQRPGSSPTTVIYE

<u>DDQRPSGVPDRFSGS</u>IDRSSNSASLTISGLTTDDEADYYC<u>QSYD`I`N`R`VI</u>FG

GGTKLTVL

The amino acids in frame were mutation sites, the amino acids corresponding to the underlined parts are CDR1 (SEQ ID NO.20), CDR2 (SEQ ID NO.21), and CDR3 (SEQ ID NO.41), respectively.

The corresponding nucleic acid sequence thereof is:

(SEQ ID NO. 42)
AATTTTATGCTGACTCAGCCCCCCTCTGTGTCGGAGTCCCCGGGGAAGACG

GTAACCATCTCCTGCACCCGCAGCAGTGGGAACATTGCCAGCTTCTATGTG

CAGTGGTTTCAACAGCGCCCGGGCAGTTCCCCCACCACTGTGATCTATGAA

GATGACCAAAGACCCTCTGGGGTCCCTGATCGGTTCTCTGGCTCCATCGAC

AGATCGTCCAACTCTGCCTCCCTCACCATTTCTGGACTGACGACTGACGAC

GAGGCTGACTACTACTGTCAGTCTTATGAT`ATC`AAC`AAG`GTCATATTCGGC

GGAGGGACCAAGCTGACCGTCCTA

The amino acid sequence of heavy chain variable region of anti-CD137 14# mAb new is:

(SEQ ID NO. 14)
QVQLQQSGPGLVKPSQTLSLTCAISGDSVS<u>SNSAAWN</u>WIRQSPSRGLEW

LG<u>RTYYRSKWYNDYAPSVES</u>RITINPDTSKNQFSLQLSSVTPEDTAVYY

CARD<u>PPYVLSTFDI</u>WGQGTMVTVSS

The amino acids corresponding to the underlined parts are CDR1 (SEQ ID NO.15), CDR2 (SEQ ID NO.16), and CDR3 (SEQ ID NO.17), respectively.

The corresponding nucleic acid sequence thereof is:

(SEQ ID NO. 18)
CAGGTACAGCTGCAGCAGTCAGGTCCAGGACTGGTGAAGCCCTCGCAGAC

CCTCTCACTCACCTGTGCCATCTCCGGGGACAGTGTTTCTAGCAACAGTG

CTGCTTGGAACTGGATCAGGCAGTCCCCATCGAGGGGCCTTGAGTGGCTG

GGAAGGACATACTACAGGTCCAAGTGGTATAATGATTATGCACCATCTGT

GGAAAGTCGAATAACCATCAACCCAGACACATCCAAGAACCAGTTCTCCC

TGCAGCTGAGCTCTGTGACTCCCGAGGACACGGCTGTGTACTACTGTGCA

AGAGACCCTCCTTATGTGCTCAGTACTTTTGATATCTGGGGCCAAGGGAC

AATGGTCACCGTCTCCTCA

The amino acid sequence of light chain variable region of anti-CD137 14# mAb new is:

(SEQ ID NO. 43)
NFMLTQPPSVSESPGKTVTISC<u>TRSSGNIASFYVQ</u>WFQQRPGSSPTTVIY<span style="border:1px solid">D</span>

DD<u>QRPSGVPDRFSGSIDRSSNSASLTISGLTTDDEADYYCQSYD<span style="border:1px solid">INK</span>V</u>IFG

GGTKLTVL

The amino acids in frame were mutation sites, the amino acids corresponding to the underlined parts are CDR1 (SEQ ID NO.20), CDR2 (SEQ ID NO.35), and CDR3 (SEQ ID NO.41), respectively.

The corresponding nucleic acid sequence thereof is:

(SEQ ID NO. 44)
AATTTTATGCTGACTCAGCCCCCCTCTGTGTCGGAGTCCCCGGGGAAGACG

GTAACCATCTCCTGCACCCGCAGCAGTGGGAACATTGCCAGCTTCTATGTG

CAGTGGTTTCAACAGCGCCCGGGCAGTTCCCCCACCACTGTGATCTAT<span style="border:1px solid">GAC</span>

GATGACCAAAGACCCTCTGGGGTCCCTGATCGGTTCTCTGGCTCCATCGAC

AGATCGTCCAACTCTGCCTCCCTCACCATTTCTGGACTGACGACTGACGAC

GAGGCTGACTACTACTGICAGTCTTATGAT<span style="border:1px solid">ATC</span>AAC<span style="border:1px solid">AAG</span>GTCATATTCGGC

GGAGGGACCAAGCTGACCGTCCTA

Example 7. Identification of Characteristics of Anti-hCD137 14# mAb and Variants Thereof 7.1 Identification of Specifically Binding to hCD137 (FACS):

HEK293 cells expressing hCD137-EGFP, hOX40-EGFP, hCD27-EGFP and hGITR-EGFP constructed in Example 1 were resuspended in 0.5% PBS-BSA Buffer and anti-hCD137 C14 mAb protein was added, the negative control was hIgG Fc protein, then the mixture was incubated on ice for 20 min. After washing, a secondary antibody anti-hIg-PE (eBioscience™) was added and incubated on ice for 20 min. After washing, the cells were resuspended in 500 μL 0.5% PBS-BSA Buffer and detected by flow cytometry. Results were shown in the figure. As shown in FIG. 6, anti-hCD137 C14 mAb was able to bind to hCD137-EGFP cells, but unable to bind to several other EGFP cells (hOX40-EGFP-293F, hCD27-EGFP-293F and hGITR-EGFP-293F), showing good capability of specificity.

Figure 7:
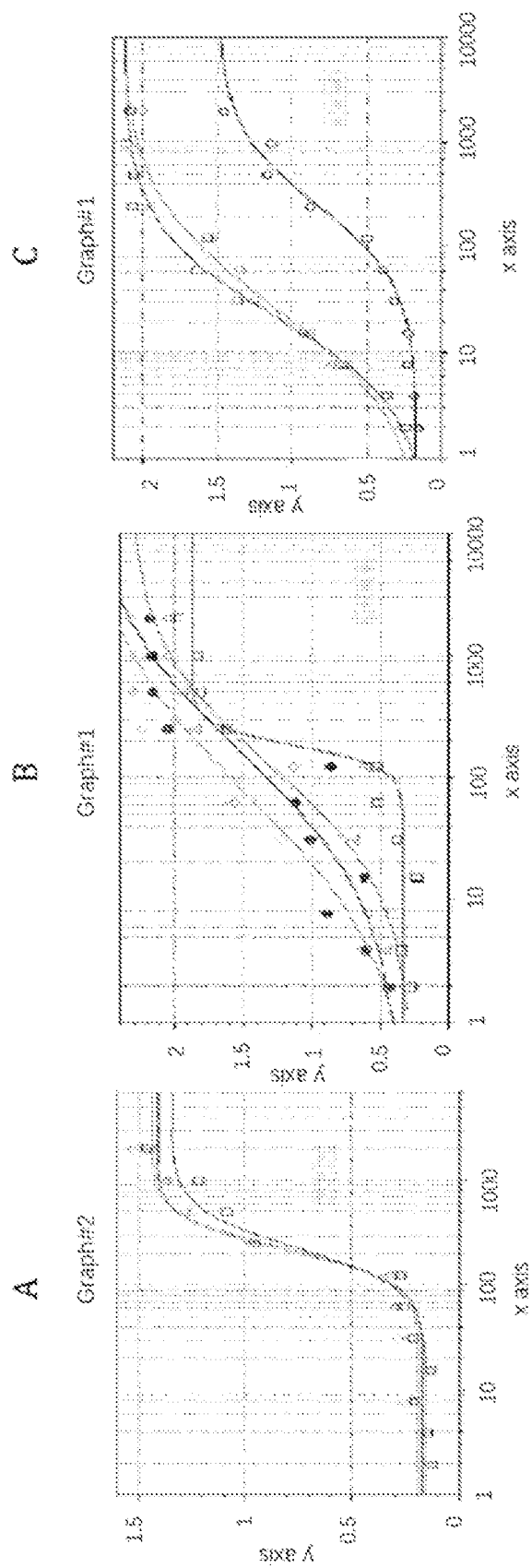
FIG. 7 is a graph showing the binding capacity of anti-hCD137 antibody to hCD137.

7.2 Detection on the Capacity of Binding to hCD137 Proteins (ELISA):

hCD137-muFc was diluted to 2 μg/mL with coating buffer (50 mM $Na_2CO_3$, $NaHCO_3$ pH 9.6), 100 μL/well, overnight at 4° C. After washing, the plates were blocked with 3% BSA-PBS for 1 h at 37° C. C14 mAb and variants thereof were respectively diluted from 2000 ng/mL and were diluted 2-fold to a total of 11 concentrations, with the diluent (1% BSA-PBS) as a control, and incubated for 2h at 37° C. Goat anti-hIgG-HRP (Goat anti-hIgG-HRP conjugated) was added and incubated for 1 h at 37° C. The soluble one-component TMB substrate developing solution was added, and the developing was performed in dark at room temperature for 5-10 min. 2N $H_2SO_4$ 50 μL/well was added to terminate the color development reaction. The $OD_{450\ nm-650\ nm}$ values were read on MD SpectraMax Plus 384 microplate Reader™, and SoftMax Pro v5.4™ was used for data processing and diagraph analysis, with the results shown in FIG. 7.

As shown in FIG. 7A, the binding of the antibody and the antigen was not affected when H54 and H57 sites of the heavy chain were mutated at the same time, and meanwhile, the affinity between the antibody and the antigen did not increase; as shown in FIG. 7B, the mutation of the light chain could increase the affinity between the antibody and the antigen, especially when L93 and L95 sites were mutated at the same time. It can be seen from FIG. 7C that, the affinities of anti-CD137 14# L93L95mAb and anti-CD137 14# mAb new with hCD137 were similar to each other.

7.3 Detection on the Capacity of Binding to hCD137 Proteins (SPR):

The binding kinetics of anti-hCD137 antibody against the recombinant human CD137 were measured by surface plasmon resonance (SPR) process using a BIAcore X100 ™ instrument. Anti-hFc antibody (not cross-identifying mouse Fc) was conjugated on CM5 chip, CD137-muFc was diluted to 5 nM with running buffer and captured as a ligand by the antibody on the chip. CD137-muFc was diluted with running buffer to 1000-31.6 nM (C14Mab) or 100-3.16 nM (C14 Mab new), diluted twice to a total of 6 concentrations. The injection time was 180s, the dissociation time was 1800s and the regeneration time was 60s. The running buffer was HBS-EP+, and the regeneration buffer was 10 mM glycine-HCl (pH 2.0). The association rate ($K_{on}$) and the dissociation rate ($K_{off}$) were calculated using a simple one-to-one one Languir™ binding model (BIAcore Evaluation Software version 3.2™). The equilibrium dissociation constant (KD) was calculated as the ratio of $K_{off}/K_{on}$. The measured binding affinities of anti-hCD137 antibodies were seen in Table 3.

TABLE 3

| Detection of Binding Kinetics between Anti-hCD137 Antibody and hCD137 | | | |
| --- | --- | --- | --- |
| Name | $K_{on}$ (1/Ms) | $K_{off}$ (1/s) | $K_D$ (M) |
| C14 mAb | 1.253E+4 | 1.741E−4 | 2.992E−8 |
| C14 mAbnew | 3.38E+05 | 9.07E−04 | 2.68E−09 |

Figure 8:
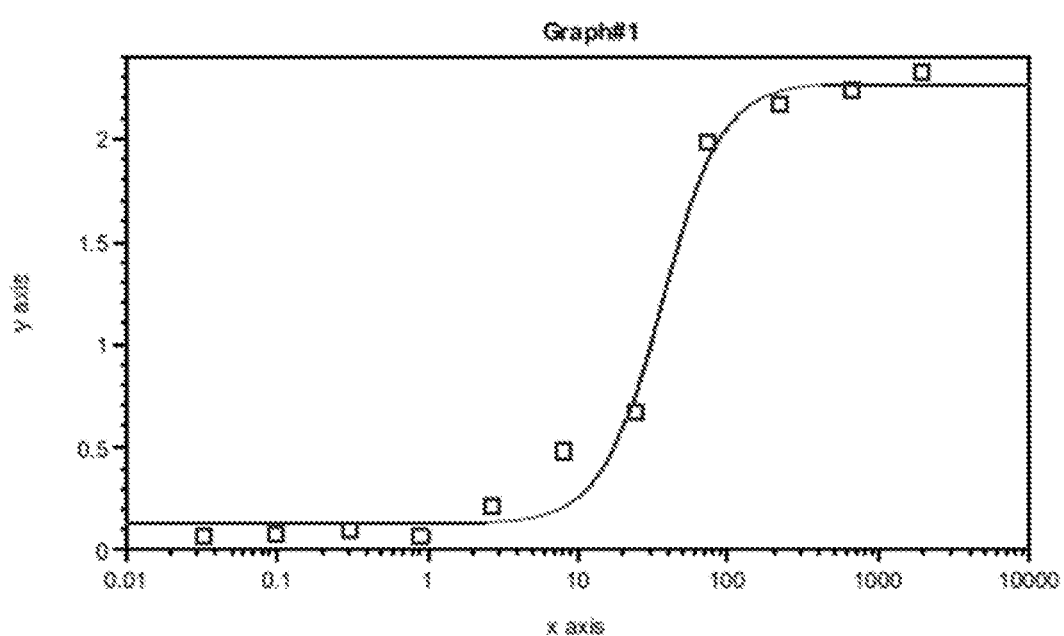
FIG. 8 is a graph showing the binding capacity of anti-CD137 antibody to Rhesus monkey CD137.

7.4 Detection on the Capacity of Binding to Rhesus Monkey CD137 Proteins (ELISA):

RhCD137-muFc was diluted to 5 µg/mL 100 µL/well, with coating buffer (50 mM $Na_2CO_3$, $NaHCO_3$ pH 9.6), overnight at 4° C. After washing, the plates were blocked with 3% BSA-PBS for 1 h at 37° C. Anti-hCD137 14# mAbnew antibodies were respectively diluted from 2000 ng/mL and were diluted 3-fold, with the diluent (1% BSA-PBS) as a control, and incubated for 2 h at 37° C. Goat anti-hIgG-HRP conjugated was added and incubated for 1 h at 37° C. The soluble one-component TMB substrate developing solution was added, and the developing was performed in dark at room temperature for 5-10 min. 2N $H_2SO_4$ 50 µL/well was added to terminate the color development reaction. The $OD_{450\ nm-650\ nm}$ values were read on MD SpectraMax Plus 384 microplate Reader™, and SoftMax Pro v5.4™ was used for data processing and diagraph analysis, with the results shown in FIG. 8, in which it can be seen that anti-hCD137 14# mAb new may bind to CD137 of rhesus monkey.

7.5 Detection of CD137 Protein Binding in Competition with CD137L (FACS)

Figure 9:
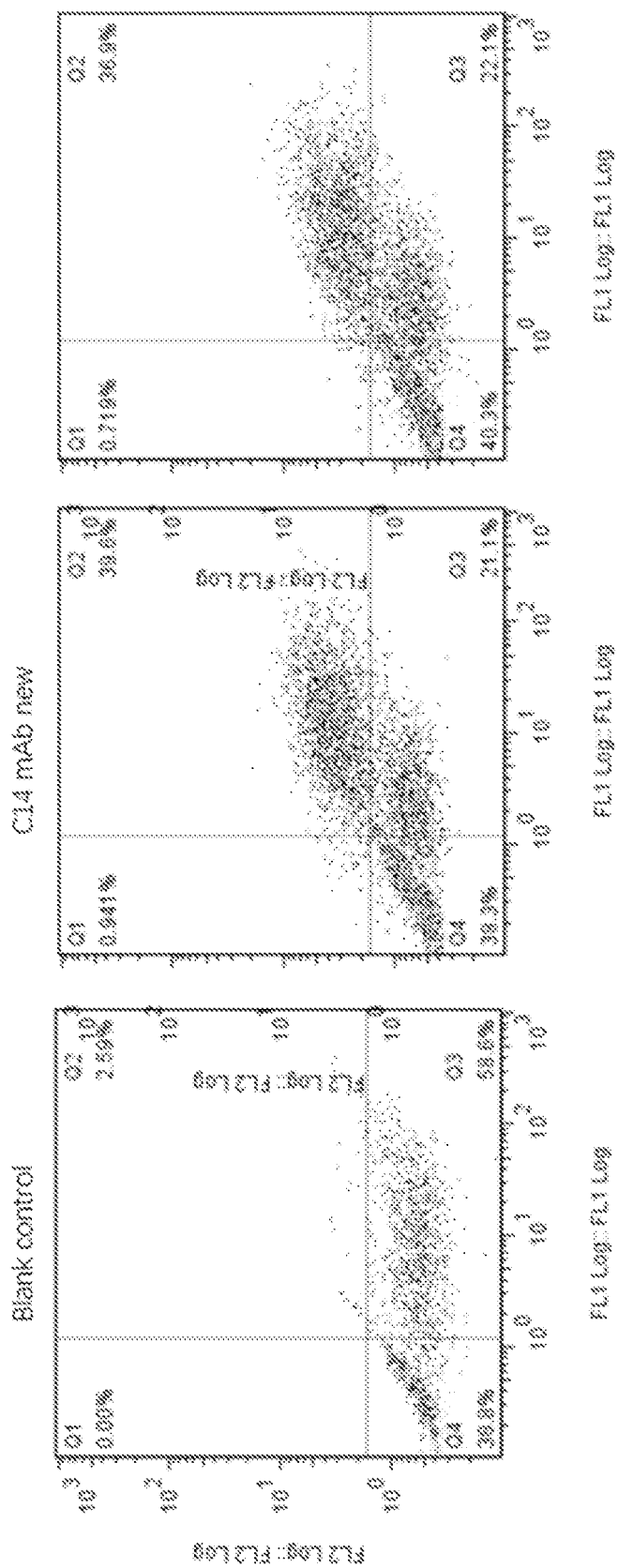
FIG. 9 is a graph showing the results of anti-CD137 antibody and hCD137L competitively binding to hCD137.

It was detected whether anti-CD137 14# mAbnew can block the binding of CD137L and CD137 protein expressed on the cell surface. Taking $5×10^5$ CD137L-EGFP cells constructed in Example 1, to the reaction system were added 10 µg/mL CD137-muFc protein and 20 µg/mL anti-CD 137 C14# mAbnew antibody, which were incubated on ice for 20 min, washed twice, and then anti-mIg-PE secondary antibody was added to stain and incubated on ice for 20 min, washed twice and then the cells were stored in PBS containing 0.5% BSA, with the addition of CD137-muFc while no addition of antibodies as the control. The staining was detected by a flow cytometer, with results shown in FIG. 9, wherein X-axis represents the fluorescence intensity of EGFP, Y-axis represents the fluorescence intensity of PE. It can be seen from the results that, anti-CD137 14# mAbnew here did not block the binding between CD137L and CD137 protein.

Example 8. Determination on the Activity of Anti-CD137 C14 mAb Agonist

Figure 10:
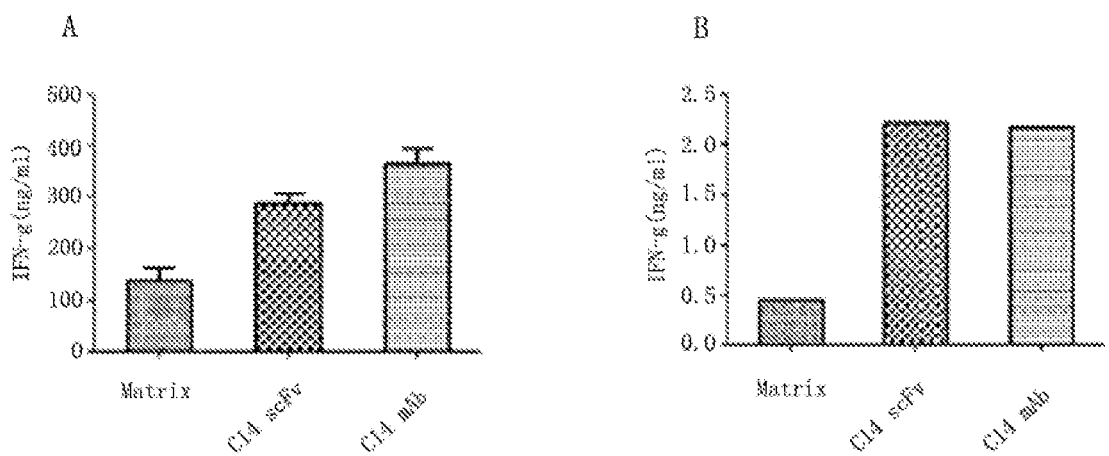
FIG. 10 shows the detection of the capacity of anti-CD137 C14# mAb stimulating PBMC or CD8+ T cells to secrete IFN-γ.

Peripheral blood mononuclear cells (PBMCs) were isolated from peripheral blood concentrated leukocytes of healthy donors by the density gradient centrifugation using human lymphocyte separation fluid (Tianjin Hao Yang™) and seeded into RPMI™ complete medium. 96-well plates were pre-coated with 50 µL of 10 µg/mL anti-CD3 and 0.5 µg/mL soluble anti-CD28 overnight at 4° C. Experimental groups were coated with 50 µL of 2 µg/mL C14 ScFv or C14 mAb and cross-link (Jackson ImmunoResearch Laboratories: 109-006-008) with a final concentration of 2 µg/mL, the negative control was RPMI™ complete medium. The amount of PBMCs was $2×10^5$/well, the cells were cultured for five days and then the supernatant was taken. The level of IFN-γ in the supernatant of PBMC was detected by the IFN-γ ELISA detection kit (eBioscience™) and the results were shown in FIG. 10A. It can be seen from the results that anti-CD137 14# ScFv and mAb both could upregulate the level of IFN-γ secreted by the activated PBMC.

Peripheral blood mononuclear cells (PBMCs) were isolated from peripheral blood concentrated leukocytes of healthy donors by the density gradient centrifugation using human lymphocyte separation fluid (Tianjin Hao Yang™) and seeded into RPMI™ complete medium. CD8+ T cells were isolated from PBMC by using the magnetic bead separation kit (Miltenyi Biotec:130-096-533), according to the method in the specification. They were weighed and resuspended in RPMI™ complete medium, with a concentration of 2 million/mL. The isolated CD8+ T cells were stimulated with 1 µg/mL anti-CD3 and 0.2 µg/mL anti-CD28 to be activated. Into the experimental groups were added 2 µg/mL C14ScFv or C14 mAb and cross-link (Jackson ImmunoResearch Laboratories: 109-006-008) with a final concentration of 2 µg/mL, the negative control was RPMI™ complete medium. The cells were cultured for five days and then the supernatant was taken. The level of IFN-γ in the supernatant of CD8+ T cells was detected by the IFN-γ ELISA detection kit (eBioscience™) and the results were shown in FIG. 10B. It can be seen from the results that anti-CD137 14# ScFv and mAb could both increase the capacity of CD8+ T cells secreting IFN-γ.

Example 9. Inhibition of Tumor Growth by Anti-CD137 Antibody in Mice

Figure 11:
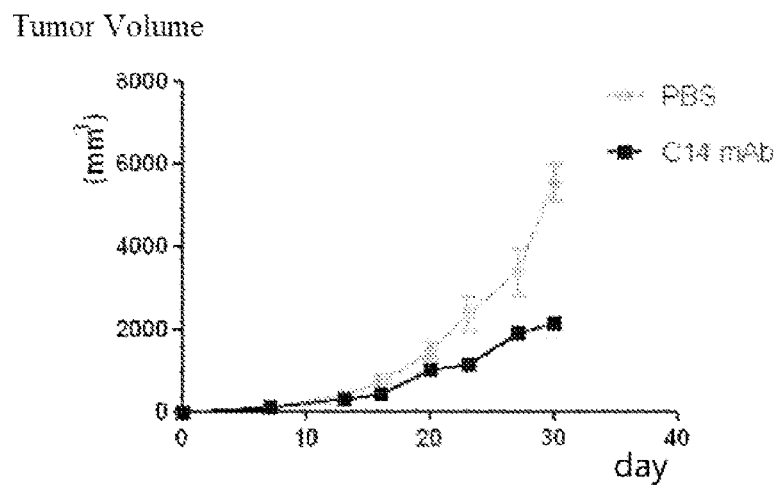
FIG. 11 shows the experimental results of anti-CD137 C14# mAb significantly inhibiting the growth of tumors.

The NOD-SCID mouse tumor models implanted with tumor cells PC-3 and human PBMCs were used to evaluate the in vivo efficacy of anti-CD137 antibody. Mice were injected subcutaneously (SC) with PC-3 $5×10^6$ (ATCCCRL-1435™) and human peripheral blood mononuclear cells $2.5×10^6$ (PBMCs) on day 0 and injected intraperitoneally with 1 mg/kg C14 mAb on day 0 and day 7, PBS was used as the negative control. Tumor formation was observed twice a week and the length diameters and short diameters of the tumors were measured with a vernier caliper. The tumor volume was calculated and the tumor growth curve was plotted. The results were shown in FIG. 11, and it could be seen that the antibody C14 mAb could significantly inhibit the tumor growth.

Example 10. Detection on the Stability of Anti-CD137 14# mAb 10.1 the Stability of Anti-CD137 14# mAb was Detected Using an Accelerated Stability Test at 45° C.

Figure 12:
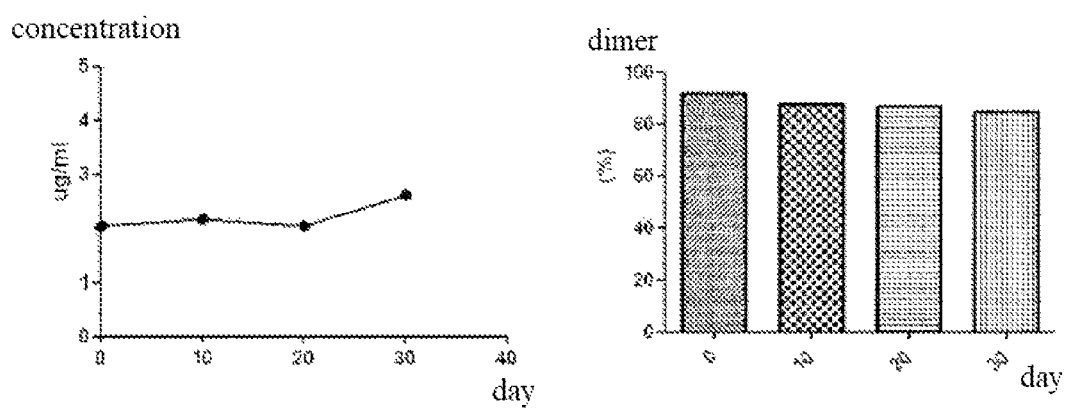
FIG. 12 shows the experimental results of anti-CD137 C14# mAb accelerating the stability.

An accelerated stability test at 45° C. was performed on anti-CD137 14# mAb, the specific experimental method was as follows: the anti-CD137 14# mAb purified with Protein A™ in one step was dissolved in PBS (pH7.4) and concentrated to 2 mg/ml, 100 µg of antibody was placed in a 200 µL PCR tube in 45° C. water bath, and sampled on day 0, day 10, day 20 and day 30 for A280 detection and SEC-HPLC analysis, with the results shown in FIG. 12. Wherein Fig. A is a graph of antibody concentration over time, and it can be seen that the concentrations of samples collected at different time points did not change significantly; Fig. B is the percentage of the antibody dimer over time, and it can be seen that as time increases, the proportion of the antibody dimer was slightly reduced, and no aggregate was formed.

10.2 Detection on the Stability of Anti-CD137 14# mAb by Differential Scanning Calorimeter (DSC)

The thermal stability of anti-CD137 14# mAb was detected by DSC method. In order to correctly complete the test by DSC, the scanning results of a single buffer solution and a buffer solution containing protein were collected.

Figure 13:
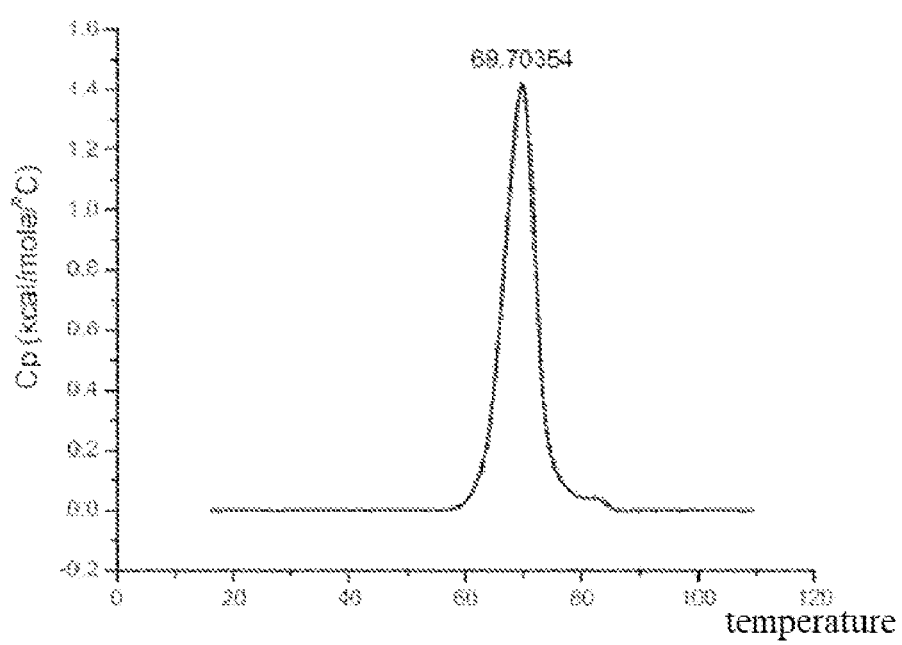
FIG. 13 is a graph showing the results of the thermal stability of anti-CD137 C14# mAb detected by DSC method.

The anti-CD137 14# mAb protein was diluted to 1 mg/mL (PBS buffer). Data was collected under the following conditions: the DSC was set to scan at 10-110° C. at the scanning speed of 100° C./h, and there was equilibrium of 15 minutes before each scanning. The volume of DSC sample chamber was 0.5 mL. After collection of the scanning results of the buffer and the protein, the scanning result of the protein can be subtracted from the scanning result of the buffer. The concentration of protein in the sample was obtained to correct the concentration in each scanning, thus obtained the Tm value of anti-CD137 14# mAb, with the results shown in FIG. 13, from which it can be seen that the Tm value of anti-CD137 14# mAb was 69.70° C.

It should be appreciated by those skilled in the art that, the detailed description of the present invention has been described herein, but various modifications may be made thereto without departing from the spirit and scope of the invention. Hence, the detailed description and examples of the present invention should not be considered as limiting the scope of the present invention. The present invention is limited only by the claims appended hereto.

What is claimed is:

1. An antibody specifically binding to CD137 or an antigen-binding portion thereof, comprising a heavy chain variable region and a light chain variable region, wherein:
said heavy chain variable region comprises a CDR1 having a sequence as set forth in SEQ ID NO.5, a CDR2 having a sequence as set forth in SEQ ID NO.6, and a CDR3 having a sequence as set forth in SEQ ID NO.7; and
said light chain variable region comprises a CDR1 having a sequence as set forth in SEQ ID NO.10, a CDR2 having a sequence as set forth in SEQ ID NO.11, and a CDR3 having a sequence as set forth in SEQ ID NO.12;
or
said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and
said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.22;
or
said heavy chain variable region comprises a CDR1 having a sequence as set forth in SEQ ID NO.15, a CDR2 having a sequence as set forth in SEQ ID NO.29, and a CDR3 having a sequence as set forth in SEQ ID NO.17; and
said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.22;
or said heavy chain variable region comprises a CDR1 having a sequence as set forth in SEQ ID NO.32, a CDR2 having a sequence as set forth in SEQ ID NO.16, and a CDR3 having a sequence as set forth in SEQ ID NO.17; and
said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.22;
or
said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and
said light chain variable region comprises a CDR1 having a sequence as set forth in SEQ ID NO.20, a CDR2 having a sequence as set forth in SEQ ID NO.35, and a CDR3 having a sequence as set forth in SEQ ID NO.22;
or
said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and
said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.38;
or
said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and
said light chain variable region comprises a CDR1 having a sequence as set forth in SEQ ID NO.20, a CDR2 having a sequence as set forth in SEQ ID NO.21, and a CDR3 having a sequence as set forth in SEQ ID NO.41;
or
said heavy chain variable region comprises a CDR1 having a sequence as set forth in SEQ ID NO.15, a CDR2 having a sequence as set forth in SEQ ID NO.16, and a CDR3 having a sequence as set forth in SEQ ID NO.17; and
said light chain variable region comprises a CDR1 having a sequence as set forth in SEQ ID NO.20, a CDR2 having a sequence as set forth in SEQ ID NO.35, and a CDR3 having a sequence as set forth in SEQ ID NO.41.

2. The antibody or an antigen-binding portion thereof according to claim 1, wherein:
said heavy chain comprises a variable region having a sequence as set forth in SEQ ID NO.4; and
said light chain comprises a variable region having a sequence as set forth in SEQ ID NO.9;
or
said heavy chain comprises a variable region having a sequence as set forth in SEQ ID NO.14; and
said light chain comprises a variable region having a sequence as set forth in SEQ ID NO.19;
or
said heavy chain comprises a variable region having a sequence as set forth in SEQ ID NO.28; and
said light chain comprises a variable region having a sequence as set forth in SEQ ID NO.19;
or
said heavy chain comprises a variable region having a sequence as set forth in SEQ ID NO.31; and said light chain comprises a variable region having a sequence as set forth in SEQ ID NO.19;
or
said heavy chain comprises a variable region having a sequence as set forth in SEQ ID NO.14; and
said light chain comprises a variable region having a sequence as set forth in SEQ ID NO.34;
or
said heavy chain comprises a variable region having a sequence as set forth in SEQ ID NO.14; and
said light chain comprises a variable region having a sequence as set forth in SEQ ID NO.37;
or
said heavy chain comprises a variable region having a sequence as set forth in SEQ ID NO.14; and
said light chain comprises a variable region having a sequence as set forth in SEQ ID NO.40;
or
said heavy chain comprises a variable region having a sequence as set forth in SEQ ID NO.14; and
said light chain comprises a variable region having a sequence as set forth in SEQ ID NO.43.

3. The antibody or an antigen-binding portion thereof according to claim 1, wherein said antibody or said antigen-binding portion thereof is a complete antibody, a bispecific antibody, scFv, Fab, Fab', F(ab)$_2$ or Fv.

4. A single-chain antibody, comprising a VH, a VL and a linker peptide, wherein the VH has a sequence as set forth in SEQ ID NO.4, the VL has a sequence as set forth in SEQ ID NO.9, and the linker peptide has a sequence as set forth in SEQ ID NO.1 or the VH has a sequence as set forth in SEQ ID NO.14, the VL has a sequence as set forth in SEQ ID NO.19 and the linker peptide has a sequence as set forth in SEQ ID NO.1.

5. A pharmaceutical composition, comprising:
the antibody or an antigen-binding portion thereof of claim 1; and
a pharmaceutically acceptable carrier.

6. An isolated polynucleotide, comprising a nucleotide sequence encoding an amino acid sequence as set forth in SEQ ID NO.4, SEQ ID NO.14, SEQ ID NO.28, SEQ ID NO.31.

7. The polynucleotide according to claim 6, comprising a nucleotide sequence as set forth in SEQ ID NO.8, SEQ ID NO.18, SEQ ID NO.30, or SEQ ID NO.33.

8. An isolated polynucleotide, comprising a nucleotide sequence encoding an amino acid sequence as set forth in SEQ ID NO.9, SEQ ID NO.19, SEQ ID NO.34, SEQ ID NO.37, SEQ ID NO.40, or SEQ ID NO.43.

9. The polynucleotide according to claim 8, comprising a nucleotide sequence as set forth in SEQ ID NO.13, SEQ ID NO.23, SEQ ID NO.36, SEQ ID NO.39, SEQ ID NO.42, or SEQ ID NO.44.

10. A vector, containing a nucleotide sequence as set forth in SEQ ID NO.8, SEQ ID NO.18, SEQ ID NO. 30, or SEQ ID NO.33.

11. A vector, containing a nucleotide sequence as set forth in SEQ ID NO.13, SEQ ID NO.23, SEQ ID NO.36, SEQ ID NO.39, SEQ ID NO.42, or SEQ ID NO.44.

12. A cell, containing a nucleotide sequence as set forth in SEQ ID NO.8, SEQ ID NO.18, SEQ ID NO.30, or SEQ ID NO.33.

13. A cell, containing a nucleotide sequence as set forth in SEQ ID NO.13, SEQ ID NO.23, SEQ ID NO.36, SEQ ID NO.39, SEQ ID NO.42, or SEQ ID NO.44.

* * * * *